United States Patent
Zhou et al.

(10) Patent No.: US 11,248,022 B2
(45) Date of Patent: Feb. 15, 2022

(54) GLYPICAN-3 PEPTIDE REAGENTS AND METHODS

(71) Applicant: THE REGENTS OF THE UNIVERSITY OF MICHIGAN, Ann Arbor, MI (US)

(72) Inventors: Juan Zhou, Ann Arbor, MI (US); Thomas D. Wang, Ann Arbor, MI (US); Zhao Li, East Lansing, MI (US); Bishnu P. Joshi, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/491,117

(22) PCT Filed: Mar. 7, 2018

(86) PCT No.: PCT/US2018/021417
§ 371 (c)(1),
(2) Date: Sep. 4, 2019

(87) PCT Pub. No.: WO2018/165344
PCT Pub. Date: Sep. 13, 2018

(65) Prior Publication Data
US 2020/0010508 A1    Jan. 9, 2020

Related U.S. Application Data

(60) Provisional application No. 62/468,626, filed on Mar. 8, 2017.

(51) Int. Cl.
| | |
|---|---|
| *C07K 7/08* | (2006.01) |
| *A61K 47/69* | (2017.01) |
| *A61K 47/55* | (2017.01) |
| *A61K 49/00* | (2006.01) |
| *C07K 7/06* | (2006.01) |
| *G01N 33/58* | (2006.01) |
| *G01N 33/68* | (2006.01) |

(52) U.S. Cl.
CPC ............... *C07K 7/08* (2013.01); *A61K 47/55* (2017.08); *A61K 47/6907* (2017.08); *A61K 49/0032* (2013.01); *A61K 49/0043* (2013.01); *A61K 49/0056* (2013.01); *C07K 7/06* (2013.01); *G01N 33/582* (2013.01); *G01N 33/68* (2013.01)

(58) Field of Classification Search
CPC ............ A61K 2121/00; A61K 2123/00; A61K 47/00; A61K 47/6907; A61K 47/55; A61K 47/62; A61K 49/00; A61K 49/0032; A61K 49/0043; A61K 49/0056; A61P 35/00; C07K 7/08; C07K 7/06; C07K 1/13; G01N 33/582; G01N 33/68; G01N 2800/52; G01N 33/57438
USPC .......... 424/1.11, 1.49, 1.65, 1.69, 1.81, 1.85, 424/9.1, 9.2, 9.3, 9.4, 9.5, 9.6; 514/1, 514/1.1, 19.2, 19.3, 19.4, 19.5, 19.6, 21.3, 514/21.4, 21.5, 21.6; 530/300; 534/7, 534/10–16
See application file for complete search history.

(56) References Cited

U.S. PATENT DOCUMENTS

| | | | | |
|---|---|---|---|---|
| 5,175,343 | A | * 12/1992 | Fritzberg | ............ A61K 51/0478 534/10 |
| 8,388,937 | B2 | 3/2013 | Ahn et al. | |
| 10,138,273 | B2 | * 11/2018 | Cheng | .................... C07K 14/00 |
| 2010/0310459 | A1 | 12/2010 | Wang et al. | |
| 2015/0152147 | A1 | 6/2015 | Gosselin et al. | |
| 2017/0101442 | A1 | 4/2017 | Cheng et al. | |

FOREIGN PATENT DOCUMENTS

| | | |
|---|---|---|
| CN | 105039333 A | 11/2015 |
| WO | WO-2013/174783 A1 | 11/2013 |
| WO | WO-2014/159087 A1 | 10/2014 |
| WO | WO-2015/188934 A1 | 12/2015 |
| WO | WO-2017/096076 A1 | 6/2017 |

OTHER PUBLICATIONS

ThermoFisher Scientific, 5-FAM (5-Carboxyfluorescein), single isomer, https://www.thermofisher.com/order/catalog/product/C1359#/C1359 (Feb. 19, 2021, date retrieved) (Year: 2021).*
Chen et al, Molecular Pharmaceutics, vol. 12, pp. 2180-2188 (Year: 2015).*
Alspach, "A Gaussian Sum Approach to the Multi-Target Identification-Tracking Problem," Automatica, 11(3): 285-296 (1975).
Capurro et al., "Glypican-3: A Novel Serum and Histochemical Marker for Hepatocellular Carcinoma," Gastroenterology, 125(1):89-97 (2003).
Cheng et al., "Efficacy and safety of sorabenib in patients in the Asia-Pacific region with advanced hepatocellular carcinoma: a phase III randomised, double-blind, placebo-controlled trial," Lancet Oncol,10:25-34 (2009).
Cwirla et al., "Peptides on phage: A vast library of peptides for identifying ligands," Proc. Natl. Acad. Sci. USA, 87:6378-6382 (1990).
International Search Report and Written Opinion from International Application No. PCT/US2018/021417 filed Jun. 6, 2018.
Joshi et al., "Design and Synthesis of Near-Infrared Peptide for in Vivo Molecular Imaging of HER2," Bioconjug Chem, 27:481-494 (2016).

(Continued)

*Primary Examiner* — D. L. Jones
(74) *Attorney, Agent, or Firm* — Marshall, Gerstein & Borun LLP

(57) ABSTRACT

The present invention is directed to glypican-3-specific peptide reagents, methods for detecting hepatocellular carcinoma cells using the peptide reagents, and methods for targeting hepatocellular carcinoma cells using the peptide reagents.

20 Claims, 26 Drawing Sheets
Specification includes a Sequence Listing.

(56) References Cited

OTHER PUBLICATIONS

Khondee et al., "Targeted therapy of colorectal neoplasia with rapamycin in peptide-labeled pegylated octadecyl lithocholate micelles," J. Controlled Release, 199:114-121 (2015).
Liu et al., "Optical Imaging of Integrin αvβ3 Expression with Near-Infrared Fluorescent RGD Dimer with Tetra (ethylene glycol) Linkers," Molecular Imaging 9(1):21-29 (2010).
Llovet et al., "Sorafenib in Advanced Hepatocellular Carcinoma," N Engl J Med, 359:378-390 (2008).
Macindoe et al., "HexServer: an FFT-based protein docking server powered by graphics processors," Nucleic Acids Research, 38(S2):W445-W449 (2010).
Maluccio et al., "Recent Progress in Understanding, Diagnosing, and Treating Hepatocellular Carcinoma," Cancer J. Clin., 62(6): 394-399 (2012).
Nakatsura et al., "Glypican-3, overexpressed specifically in human hepatocellular carcinoma, is a novel tumor marker," Biochem Biophys Res Commun, 306:16-25 (2003).
Pasqualini et al., "Organ targeting in vivo using phage display peptide libraries," Nature, 380:364-366 (1996).
Pellosi et al., "Pluronic P123/F127 mixed micelles delivering sorafenib and its combination with verteporfin in cancer cells," International Journal of Nanomedicine 11:4479-4494 (2016).
Rabinsky et al., "Overexpressed Claudin-1 Can Be Visualized Endoscopically in Colonic Adenomas In Vivo," Cell Mol Gastroenterol Hepatol, 2:222-237 (2016).
Roessler et al., "A Unique Metastasis Gene Signature Enables Prediction of Tumor Relapse in Early-Stage Hepatocellular Carcinoma Patients," Cancer Res, 70:10202-10212 (2010).
Scott et al., "Searching for Peptide Ligands with an Epitope Library," Science, 249:386-390 (1990).
Shafizadeh et al., "Utility and limitations of glypican-3 expression for the diagnosis of hepatocellular carcinoma at both ends of the differentiation spectrum," Mod Pathol., 21(8):1011-1018 (2008).
Shirakawa et al., "Glypican-3 is a useful diagnostic marker for a component of hepatocellular carcinoma in human liver cancer," Int J Oncol, 34:649-656 (2009).
Svensson et al., "Crystal Structure of N-Glycosylated Human Glypican-1 Core Protein," J Biol Chem, 287:14040-14051 (2012).
Ueda et al., "Gene expression profiling of hepatitis B- and hepatitis C-related hepatocellular carcinoma using graphical Gaussian modeling," Genomics, 101:238-248 (2013).
Wang et al., "Glypican-3 expression in hepatocellular tumors: diagnostic value for preneoplastic lesions and hepatocellular carcinomas," Hum Pathol, 37:1435-1441 (2006).
Wilhelm et al., "BAY 43-9006 Exhibits Broad Spectrum Oral Antitumor Activity and Targets the RAF/MEK/ERK Pathway and Receptor Tyrosine Kinases Involved in Tumor Progression and Angiogenesis," Cancer Res, 64:7099-7109 (2004).
Xu et al., "A comparison of glypican-3 with alpha-fetoprotein as a serum marker for hepatocellular carcinoma: a meta-analysis," J. Cancer Res. Clin Oncol, 139:1417-1424 (2013).
Yamauchi et al., "The glypican 3 oncofetal protein is a promising diagnostic marker for hepatocellular carcinoma," Mod Pathol, 18:1591-1598 (2005).
Zhou et al., "EGFR Overexpressed in Colonic Neoplasic Can be Detected on Wide-Field Endoscopic Imaging," Clin Transl Gastroenterol, 6:e101, 11 pages (2015).
Zhu et al., "Enhanced glypical-3 expression differentiates the majority of hepatocellular carcinomas from benign hepatic disorders," Gut, 48: 558-564 (2001).

* cited by examiner

Figure 8
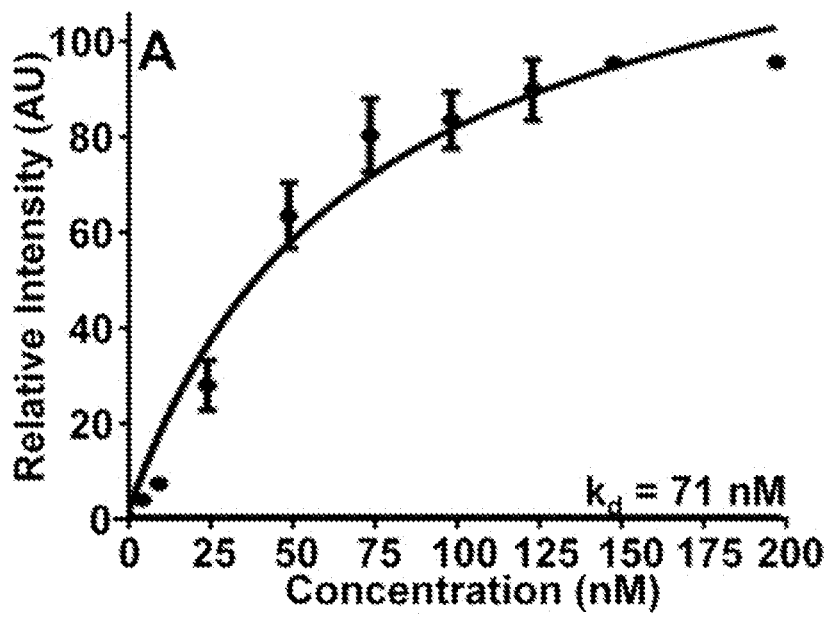
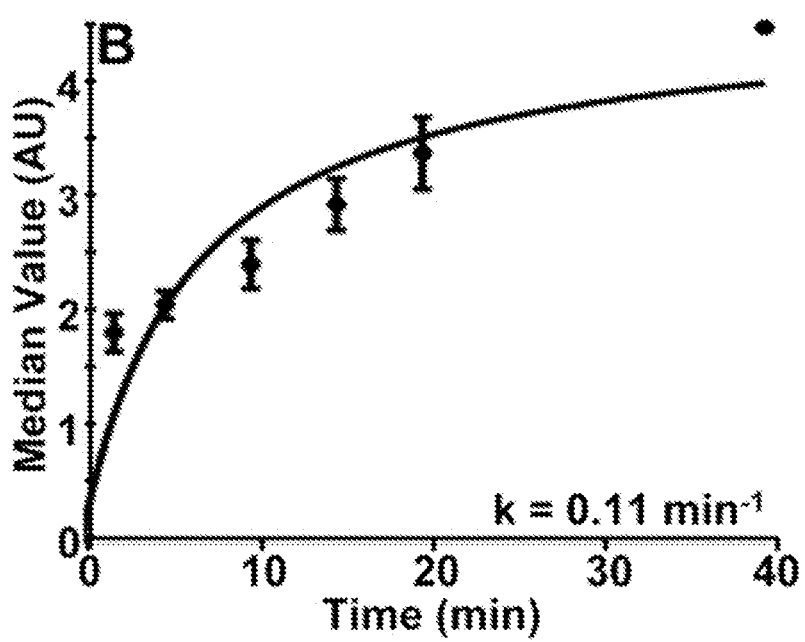

Figure 19

Diagnosis and patient medical history of human tissue samples

| ID | Diagnosis | Patient history and histology notes |
|---|---|---|
| 1 | HCC | Hep C. Background not cirrhotic. |
| 2 | HCC | NASH cirrhosis. |
| 3 | HCC | Hep C. |
| 4 | HCC | Cryptogenic cirrhosis. Includes fibro lamellar pattern. |
| 5 | HCC | Hep C. Not cirrhotic but bridging fibrosis. |
| 6 | HCC | NASH, bridging. Not cirrhotic. |
| 7 | HCC | Hep C cirrhosis. |
| 8 | HCC | Background not cirrhotic. |
| 9 | HCC | Cryptogenic cirrhosis. |
| 10 | HCC | Hep C. Not cirrhotic but bridging fibrosis. |
| 11 | HCC | Hep C cirrhosis. |
| 12 | HCC | Not cirrhotic. |
| 13 | HCC | Hep C cirrhosis. |
| 14 | HCC | HCV and HBV. |
| 15 | HCC | Alcoholic cirrhosis. |
| 16 | Cirrhosis | Alcoholic cirrhosis, no malignancy. |
| 17 | Cirrhosis | Hep C cirrhosis, no malignancy. |
| 18 | Cirrhosis | Hep C cirrhosis, no malignancy. |
| 19 | Cirrhosis | Hep C cirrhosis, no malignancy. |
| 20 | Cirrhosis | Biliary cirrhosis, no malignancy. |
| 21 | Cirrhosis | Alcoholic cirrhosis, no malignancy. |
| 22 | Cirrhosis | Hep C cirrhosis, no malignancy. |
| 23 | Cirrhosis | Hep C cirrhosis, no malignancy. |
| 24 | Cirrhosis | Hep C cirrhosis, no malignancy. |
| 25 | Cirrhosis | Alcoholic cirrhosis, no malignancy. |
| 26 | Cirrhosis | NASH cirrhosis / alpha1-Antitripin deficiency carrier. |
| 27 | Cirrhosis | Hep C cirrhosis. |
| 28 | HCA | Hepatic adenoma (area with fat). Multiple adenomas. No malignancy. |
| 29 | HCA | Hepatic adenoma (area with fat). No malignancy. |
| 30 | HCA | Hepatic adenoma (area with fat). No malignancy. |
| 31 | HCA | Normal appearing background tissue (has multiple hepatic adenomas). |
| 32 | HCA | Hepatic adenoma (small area with fat). History of lung adenocarcinoma (not in this resection). |
| 33 | HCA | Hepatic adenoma (area with fat). No malignancy. |
| 34 | HCA | Metastatic colorectal adenocarcinoma. Small amount of normal. |
| 35 | Normal | FNH, no malignancy. |
| 36 | Normal | FNH, no malignancy. |
| 37 | Normal | Hemangioma, no malignancy. |
| 38 | Normal | Hemangioma, no malignancy. |
| 39 | Normal | Hemangioma, no malignancy. |
| 40 | Normal | Hemangioma, no malignancy. |
| 41 | Normal | Hemangioma, no malignancy. |

SEQUENCE LISTING

<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 1

Ala Leu Leu Ala Asn His Glu Glu Leu Phe Gln Thr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 2

Ala Leu Leu Ala Asn His Glu Glu Leu Phe
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 3

Gly Leu His Thr Ser Ala Thr Asn Leu Tyr Leu His
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 4

Ser Gly Val Tyr Lys Val Ala Tyr Asp Trp Gln His
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 5

Val Gly Val Glu Ser Cys Ala Ser Arg Cys Asn Asn
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 6

Gln Leu Glu Leu Thr Phe His Ala Asn Leu Glu Ala
1               5                   10

```
<210> SEQ ID NO 7
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 7

Gly Gly Gly Ser Lys
1               5
```

GLYPICAN-3 PEPTIDE REAGENTS AND METHODS

This is a U.S. National Phase of International Application No. PCT/US2018/021417, filed Mar. 7, 2018, which claims priority to U.S. Provisional Patent Application No. 62/468,626 filed on Mar. 8, 2017, which is incorporated herein by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 1,717 byte ASCII (Text) file named "50687_SeqListing.txt," created on Mar. 6, 2018.

FIELD OF THE INVENTION

The present invention is directed to glypican-3-specific peptide reagents, methods for detecting hepatocellular carcinoma cells using the peptide reagents, and methods for targeting hepatocellular carcinoma cells using the peptide reagents.

BACKGROUND

Hepatocellular carcinoma (HCC) is the cause of death for an estimated 800,000 people globally, representing the second most common cause of death by cancer worldwide. HCC is primary cancer of the liver and occurs predominantly in patients with underlying chronic liver disease, such as hepatitis, and cirrhosis [Cicalese et al., *Hepatocellular Cacinoma*, Medscape (updated May 20, 2014)]. The pathophysiology of HCC is unknown and the prognosis is poor, with a 5-year survival of less than 25%. The obesity epidemic has resulted in a growing population of patients with nonalcoholic fatty liver disease which can progress to fibrosis, cirrhosis, and eventually HCC [Cicalese et al., supra; Maluccio and Covey, *Cancer J. Clin.*, 62(6): 394-399 (2012)]. Liver resection is the gold standard for patients with resectable (non-diffused) HCC. Currently, surgeons perform HCC resection with margins greater than 1 cm utilizing white light to grossly visualize the cut liver surface. However, most patients with HCC have diseased liver parenchyma, so preservation of the liver parenchyma is critical to maintain as much functional liver tissue as possible. More accurate methods of detecting tumor margins are needed to reduce the rate of recurrence without sacrificing viable tissue. Chemotherapy is currently offered as neo-adjuvant therapy for HCC, but most chemotherapeutic agents do not distinguish between malignant and normal cells, thus lead to serious adverse reactions and systemic toxicities. These drugs are expected to passively accumulate in HCC through leaky vasculature via the enhanced permeability and retention (EPR) effect. However, only 10-20% of patients have resectable livers, and of those the recurrence rate after resection is 50% after 2 years and almost 75% after 5 years (Maluccio and Covey, supra).

Sorafenib (Nexavar) is a small molecule that inhibits both the RAF/MEK/ERK pathway and tyosine kinase, and is FDA approved for treatment of HCC [Wilhelm et al., *Cancer Res*, 64:7099-7109 (2004)]. This drug is standard of care for patients with advanced HCC who are not candidates for surgery. However, sorafenib has shown only a minimal (~3 months) survival advantage over placebo in the clinic studies (SHARP) [Llovet et al., *N Engl J Med*, 359:378-390 (2008)], and sorafenib may be less effective in Asian compared with Caucasian patients, where survival duration has been found to significantly shorter (6.5 versus 7.9 months) [Cheng et al., *Lancet Oncol*,10:25-34 (2009)].

Glypican-3 (sometimes abbreviated GPC3 herein) is a heparan sulfate membrane-bound proteoglycan that is not present in normal adult liver, cirrhotic liver or benign lesions, but is found anchored to the cell surface in neoplastic hepatocytes. It is overexpressed in up to 80% of HCCs. [Capurro et al., *Gastroenterology*, 125(1): 89-97 (2003); Nakatsura et al., *Biochem Biophys Res Commun*, 306:16-25 (2003); Shafizadeh et al., *Mod Pathol.*, 21(8):1011-1018 (2008)] GPC3 promotes HCC growth by stimulating Wnt signaling and has expression levels that reflect tumor stage [Zhu et al., *Gut*, 48: 558-564 (2001)]. A number of immunochemistry studies have found strong positive staining for GPC3 in HCC and minimal staining in low-grade and high-grade dysplasia [Shirakawa et al., *Int J Oncol*, 34:649-656 (2009); Yamauchi et al., *Mod Pathol*, 18:1591-1598 (2005); Wang et al., *Hum Pathol*, 37:1435-1441 (2006)]. GPC3 has been found to be significantly more sensitive and specific for HCC than alpha-fetoprotein (AFP), a serum biomarker widely used in HCC surveillance [Xu et al., *J. Cancer Res. Clin Oncol*, 139: 1417-1424 (2013)].

New products and methods for detection and treatment of HCC are needed in the art. New products and methods would have important clinical applications for increasing the survival rate for HCC, and for reducing the healthcare costs.

SUMMARY

In one aspect, the disclosure provides a reagent comprising a peptide ALLANHEELFQT (SEQ ID NO: 1), ALLANHEELF (SEQ ID NO: 2), GLHTSATNLYLH (SEQ ID NO: 3), SGVYKVAYDWQH (SEQ ID NO: 4), or VGVESCASRCNN (SEQ ID NO: 5), or a multimer form of the peptide, wherein the reagents specifically bind to glypican-3. In some embodiments, the multimer form is a dimer. In some embodiments the peptide reagent consists essentially of the peptide or multimer form of the peptide.

In some embodiments, the reagent comprises at least one detectable label attached to the peptide or multimer form of the peptide. In some embodiments, the detectable label is detectable by microscopy, photoacoustic, ultrasound or magnetic resonance imaging. In some embodiments, the label detectable by microscopy is fluorescein isothiocyanate (FITC), Cy5, Cy5.5, or IRdye800. In some embodiments, the detectable label is attached to the peptide by a peptide linker. In some embodiments, the terminal amino acid of the linker is lysine. In some embodiment, the linker comprises the sequence GGGSK set out in SEQ ID NO: 7.

In some embodiments, the reagent comprises at least one therapeutic moiety attached to the peptide or multimer form of the peptide. In some embodiments, the therapeutic moiety is chemotherapeutic agent. In some embodiments, the therapeutic moiety is a micelle, such as a polymeric micelle encapsulating a chemotherapeutic agent (e.g., sorafenib).

In some embodiments, the regent comprises at least one detectable label attached to the peptide or multimer form of the peptide and at least one therapeutic moiety attached to the peptide or multimer form of the peptide.

In another aspect, the disclosure provides a composition comprising a reagent of the invention and a pharmaceutically acceptable excipient.

In yet another aspect, the disclosure provides methods for detecting HCC in a patient comprising the steps of administering a reagent of the invention to the liver of the patient and detecting binding of the reagent to cancerous cells.

In still another aspect, the disclosure provides methods for detecting HCC in a patient comprising the steps of administering a reagent of the invention to the patient and detecting binding of the reagent. In another aspect, the disclosure provides a method of determining the effectiveness of a treatment for liver cancer and/or cancer metastasis, or recurrence of cancer in a patient comprising the step of administering a reagent of the invention to the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, the methods further comprise obtaining a biopsy of the cells labeled by the reagent.

In yet another aspect, the disclosure provides a method for delivering a therapeutic moiety to HCC cells of a patient comprising the step of administering a reagent of the invention to the patient.

In a further aspect, the disclosure provides a kit for administering a composition of the invention to a patient in need thereof, comprising the composition, instructions for use of the composition and a device for administering the composition to the patient.

In another aspect, the disclosure provides a peptide consisting of the amino acid sequence ALLANHEELFQT (SEQ ID NO: 1), ALLANHEELF (SEQ ID NO: 2), GLHTSATN-LYLH(SEQ ID NO: 3), SGVYKVAYDWQH(SEQ ID NO: 4), or VGVESCASRCNN (SEQ ID NO: 5).

BRIEF DESCRIPTION OF THE DRAWINGS

FIGS. 1-1A-C show gene expression of GPC3 is elevated in HCC compared with non-tumor. A) Gene expression profiles from datasets GSE14520 and GSE44074 were sorted using criteria P-value<$1\times10^{-40}$, average fold-change>2, and location on cell surface to identify promising targets for HCC. Results for GPC3 show P-value=$1\times10^{-70}$ and $2\times10^{-5}$, and average fold-change of 29.261 and 2.558, respectively. B) Significant difference in GPC3 gene expression between HBV-related HCC and non-tumor specimens from n=213 specimen pairs was found, P-value<0.001 by paired t-test, from GSE14520. Data was analyzed using 22,268 probe-sets on an Affymetrix HT_U133A array platform. C) ROC curve for GSE14520 shows area-under-the curve (AUC) of 0.92 with 89% sensitivity and 92% specificity.

FIGS. 1-2A-C show gene expression of GPC3 is elevated in HCC compared with non-tumor. A) Gene expression profiles from dataset GSE14520.We used paired T-tests on log-transformed data, and obtained 1397 probe sets with P-value<$1\times10^{-40}$, of which 111 had GO terms indicating they appeared in plasma membrane, and were increased in tumors. Of these, GPC3 gave P-value=$1.1\times10^{-70}$ (5th best), and average fold-change of 29.261 (highest in tumors). We then analyzed log-transformed data for 8516 transcripts from dotted arrays measured in GEO series GSE44074, consisting of 34 HCC samples and 71 normal liver samples. A two-sample T-test gave 549 genes with P<0.001, of which 49 were increased in tumors and on plasma membrane. Of these GPC3 gave both the largest fold-change and smallest p-value (4.5 fold increase, P=$3.5\times10^{-15}$). B) Significant difference in GPC3 gene expression between HCC and non-tumor specimens from n=213 specimen pairs was found, P-value<0.001 by paired t-test, from GSE14520. Data was analyzed using 22,268 probe-sets on an Affymetrix HT_U133A array platform. Expression levels of normal and HCC liver samples were plotted with P-value<0.001 by 2-sample t-test, from GSE44074. C) ROC curve for GSE14520 shows AUC of 0.92 with 87% sensitivity and 90% specificity.

FIGS. 2A-C show validation of GPC3 overexpression in HBV-related HCC on immunohistochemistry. A) Strong staining (arrow) with anti-GPC3 antibody is seen in tumor but not in neighboring regions of cirrhosis in representative specimen of HBV-derived HCC. B) Histology (H&E) from a serial section confirms HCC (arrow) within a background of cirrhosis. C) Negative staining was found in representative non-tumor specimen (control).

FIGS. 6-1A-H show validation of specific peptide binding to GPC3 on siRNA knockdown. A) Lead candidate GPC3 peptide and B) anti-GPC3 antibody binds intensely to surface (arrows) of Hep3B cells (siCL). C,F) Control peptide shows minimal binding. Fluorescence intensity is significantly reduce in GPC3 knock down cells (siGPC3) with D) peptide and E) antibody. G) Quantified fluorescence intensities. *P=$4.1\times10^{-6}$ (peptide) and *P=$1.2\times10^{-4}$ (antibody) by paired t-test. H) Western blot of Hep3B cells.

FIGS. 6-2A-Q show validation of specific peptide binding to cells in vitro. On confocal microscopy, we observed strong fluorescence intensity from ALL*-Cy5.5 binding to the surface (arrow) of A) Hep3B and B) HepG2 human HCC cells, and minimal signal with C) SK-Hep1 cells. D-F) Minimal signal is observed with the scrambled control peptide QLE*-Cy5.5 for all cells. Strong binding (arrow) is also observed with AF488-labeled anti-GPC3 antibody used as a positive control for G) Hep3B and H) HepG2 and minimal signal with I) SK-Hep1. J) The intensity difference for Hep3B vs SK-Hep1 was significantly larger for ALL* than for the same difference for QLE* (P=$3.8\times10^{-10}$, 8.2-fold larger), and the HepG2 versus SK-Hep1 difference was also significantly larger (P=$4.6\times10^{-5}$, 3.3-fold larger). The Hep3B versus SK-Hep1 difference was also larger for antibody than QLE (P=$2.3\times10^{-8}$, 6.0-fold larger). Intensity was measured with 6 replicates per condition and fitted to an ANOVA model with terms for 9 means to log-transformed data. K) Western blot shows GPC3 expression levels for HCC cells in cytoplasm (C) and plasma membrane (M). We further validated specific peptide binding to GPC3 using siRNA knockdown. L) Western blot shows GPC3 expression level in Hep3B cells transfected with siGPC3 targeting siRNA and siCL non-targeting siRNA (control). M) ALL*-Cy5.5 (54.3±6.0) and N) AF488-labeled anti-GPC3 (37.7±7.5) binds significantly greater to the surface (arrows) of siCL treated Hep3B control cells compared to O, P) siGPC3 knockdown cells (14.7±1.5 and 8.8±2.7 respectively). Q) Quantified fluorescence intensities. The siCL vs siGPC3 difference was 7.4 times bigger for ALL than the same difference for QLE ($P=7.8\times10^{-5}$), and the difference for antibody was 8.9 times bigger than for QLE ($P=2.5\times10^{-5}$), by ANOVA on log-transformed data. Results are an average of 6 images collected independently.

FIGS. 8A-B show GPC3 peptide binding properties. A) Binding affinity (apparent dissociation constant) for ALL*-Cy5.5 to Hep3B cells is found to be $k_d=71$ nM, $R^2=0.97$. B) Binding kinetics (apparent association time constant) for ALL*-Cy5.5 to Hep3B cells is found to be $k=0.11^{-1}$ (onset of 9.1 min). Both results are representative of 3 independent measurements.

FIGS. 11-1A-L show in vivo laparoscopic images of HCC xenograft tumors. Representative A) fluorescence B) reflectance images were collected with the NIR laparoscope 2 hours after intravenous injection of the GPC3-targeting peptide, QRH*-Cy5.5, in Hep3B xenograft bearing mice are shown. C) Heat map digital image that rectifies imaging distance was generated by taking the ratio between corresponding fluorescence and reflectance images pixel by pixel. D) Region of interest was segmented by automatic imaging processing from ratio image by Otsu's method. E-H) The same set of images were collected with scrambled peptide*-Cy5.5 in a different tumor. I) White light images of mouse injected with targeting peptide ALL*-Cy5.5 and J) scrambled peptide*-Cy5.5. K) Immunohistochemistry staining of resected HCC tumor xenograft with anti-GPC3 antibody. L) Representative confocal fluorescence microscopy of excised tumor sections are shown for ALL*-Cy5.5 at 40× magnification. Note intense staining of ALL*-Cy5.5 to surface of Hep3B human HCC cells (arrow head).

FIGS. 11-2A-L show in vivo laparoscopic images of HCC xenograft tumors. A) Representative white light images of mouse injected with ALL*-Cy5.5 and D) QLE*-Cy5.5. B) Fluorescence C) reflectance images were collected with the NIR laparoscope 2 hours after intravenous injection of ALL*-Cy5.5. G) Heat map corrects for imaging distance by taking the ratio between co-registered fluorescence and reflectance images. H) Region of interest was segmented by imaging processing algorithm using ratio image. I) Immunofluorescence image of fresh resected HCC tumor xenograft 2 hours after ALL*-Cy5.5 injection. E-F, J-K) The same set of images were collected with scrambled peptide QLE*-Cy5.5 in a different tumor. L) Target-to-background ratio of ALL*-Cy5.5 (8.3±1.3) is significantly higher ($P=3.8\times10^{-8}$ on log-transformed data, 2.8-fold larger) than that of QLE*-Cy5.5 (3.0±0.7), by two-sample t-test with n=8 mice in each group.

FIG. 19 shows a table of diagnosis and patient medical history of human tissue samples for 41 biopsies diagnosed by pathologist for samples used in FIG. 16.

FIGS. 20-1A-C shows a peptide-labeled polymeric micelle. A) Biochemical structure shows encapsulation of hydrophobic drug partitioned in micelle core. B) Expanded view of dashed box shows assembly of octadecyl lithocholate, PEG, and peptide. PEG is used to improve serum stability. C) Transmission electron microscopy (TEM) shows the nanostructure of peptide-labeled polymeric micelles.

FIGS. 20-2A-C show a GPC3 peptide-labeled polymeric micelle. A) Biochemical structure of lead, candidate GPC3* peptide (the ALL peptide) attached via a GGGSK linker to Cy5.5 fluorophore is shown, in the Figure referred to as GPC3*-Cy5.5. B) The polymeric nanocarrier encapsulating sorafenib will be labeled with the optimized GPC3* peptide for use as a targeting ligand. C) The GPC3* peptide is attached via PEG to D-α tocopherol succinate in formulation of the targeted nanocarrier.

DESCRIPTION

Figure 1:
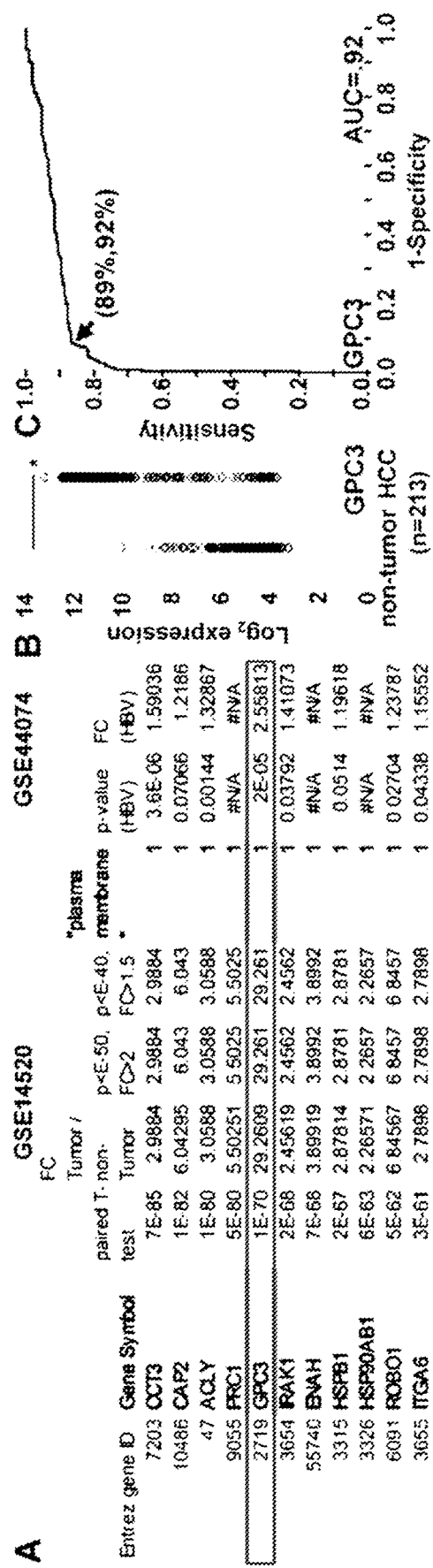

Image-guided surgery that targets overexpression of molecules that are specific for HCC can help achieve a balance between complete tumor resection and maintenance of liver function. Targeted imaging can also help maximize the remaining volume of "normal" liver parenchyma to optimize post-operative function. In addition, imaging targets specific for HCC can serve as important biomarkers for evaluating patient prognosis. Imaging reagents can provide a biological basis for disease detection, prognosis, guide therapy, and monitor treatment response. Antibodies have been most commonly used, however they are large in size, high in molecular weight, and have long plasma half-lives, all leading to increased background on imaging. Peptides are attractive imaging tools, with a small size and low molecular weight that result in improved properties for deep tissue imaging inaccessible to antibodies. Peptides are less immunogenic, clear from non-target tissues to reduce background, and can be synthesized for improved binding affinity. All of this promotes deep tissue penetration and effective targeting.

In one aspect, the invention provides peptides that bind to glypican-3 expressed on dysplastic cells and/or cancerous cells. The peptides include, but are not limited to, the peptides ALLANHEELFQT (SEQ ID NO: 1), ALLANHEELF (SEQ ID NO: 2), GLHTSATNLYLH(SEQ ID NO: 3), SGVYKVAYDWQH(SEQ ID NO: 4), or VGVESCASRCNN (SEQ ID NO: 5).

In a further aspect, the invention provides reagents comprising a peptide of the invention. A "peptide reagent" of the invention comprises at least two components, a peptide of the invention and another moiety attached to the peptide. The only component of the reagent that contributes to binding of glypican-3 is the peptide of the invention. In other words, the reagent "consists essentially of" a peptide of the invention. In some embodiments, the other moiety comprises amino acids but the peptide of the invention is not linked to those amino acids in nature and the other amino acids do not affect binding of the peptide to glypican-3. Moreover, the other moiety in a reagent contemplated herein is not a phage in a phage display library or a component of any other type of peptide display library.

In some embodiments, the reagents comprise at least one detectable label as a moiety attached to a peptide of the invention. The detectable label may be detectable, for example, by microscopy, ultrasound, PET, SPECT, or magnetic resonance imaging. In some embodiments the label detectable by microscopy is fluorescein isothiocyanate (FITC), Cy5, Cy5.5 and IRdye800.

In some embodiments, the detectable label is attached to a peptide of the invention by a peptide linker. The terminal amino acid of the linker can be a lysine such as in the exemplary linker GGGSK (SEQ ID NO: 7).

In some embodiments, the reagents comprise at least one therapeutic moiety attached to a peptide of the invention. The therapeutic moiety may be a chemopreventative or chemotherapeutic agent. In certain embodiments, the chemotherapeutic moiety is celecoxib, 5-fluorouracil, and/or chlorambucil. In some embodiments, the therapeutic moiety is a micelle encapsulating a therapeutic moiety. In certain embodiments, the micelle encapsulates sorafenib.

In some embodiments, the regent comprises at least one detectable label attached to the peptide or multimer form of the peptide, and at least one therapeutic moiety attached to the peptide or multimer form of the peptide.

In yet a further aspect, the invention provides a composition comprising a reagent of the invention and a pharmaceutically acceptable excipient.

In still a further aspect, the invention provides a method for specifically detecting HCC in a patient comprising the steps of administering a reagent of the invention attached to a detectable label to the patient and detecting binding of the reagent to HCC cells. In some embodiments, the detectable binding takes place in vivo. In others, the detectable binding takes places in vitro. In still others, the detectable binding takes place in situ.

The phrase "specifically detects" means that the reagent binds to and is detected in association with a type of cell, and the reagent does not bind to and is not detected in association with another type of cell at the level of sensitivity at which the method is carried out.

In an additional aspect, the invention provides a method of determining the effectiveness of a treatment for HCC and/or cancer metastasis, or recurrence of cancer in a patient comprising the step of administering a reagent of the invention attached to a detectable label to the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, a decrease of 5% is indicative of effective treatment. In other embodiments, a decrease of about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or more is indicative of effective treatment. In some embodiments, the method further comprises obtaining a biopsy of the cells labeled by the reagent.

In another aspect, the invention provides a method for delivering a therapeutic moiety to a patient comprising the step of administering a reagent of the invention attached to a therapeutic moiety to the patient.

In yet another aspect, the invention provides a method for delivering a therapeutic moiety to HCC cells of a patient comprising the step of administering a reagent of the invention attached to a therapeutic moiety to the liver of the patient.

In still another aspect, the invention provides a kit for administering a composition of the invention to a patient in need thereof, where the kit comprises a composition of invention, instructions for use of the composition and a device for administering the composition to the patient.

Linkers, Peptides and Peptide Analogs

As used herein, a "linker" is a sequence of amino acids located at the C-terminus of a peptide of the disclosure. In some embodiments, the linker sequence terminates with a lysine residue.

In some embodiments, the presence of a linker results in at least a 1% increase in detectable binding of a reagent of the invention to HCC cells compared to the detectable binding of the reagent in the absence of the linker. In various aspects, the increase in detectable binding is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 100-fold or more.

The term "peptide" refers to molecules of 2 to 50 amino acids, molecules of 3 to 20 amino acids, and those of 6 to 15 amino acids. Peptides and linkers as contemplated by the invention may be 5 amino acids in length. In various aspects, a polypeptide or linker may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids in length.

Exemplary peptides are, in various aspects, randomly generated by methods known in the art, carried in a polypeptide library (for example and without limitation, a phage display library), derived by digestion of proteins, or chemically synthesized. Peptides exemplified in the present disclosure have been developed using techniques of phage display, a powerful combinatorial method that uses recombinant DNA technology to generate a complex library of polypeptides for selection by preferential binding to cell surface targets [Scott et al., *Science*, 249:386-390 (1990)]. The protein coat of bacteriophage, such as the filamentous M13 or icosahedral T7, is genetically engineered to express a very large number ($>10^9$) of different polypeptides with unique sequences to achieve affinity binding [Cwirla et al., *Proc. Natl. Acad. Sci. USA*, 87:6378-6382 (1990)]. Selection is then performed by biopanning the phage library against cultured cells and tissues that over express the target. The DNA sequences of these candidate phage are then recovered and used to synthesize the polypeptide [Pasqualini et al., *Nature*, 380:364-366 (1996)]. The polypeptides that preferentially bind to GPC3 are optionally labeled with fluorescence dyes, including but not limited to, FITC, Cy 5.5, Cy 7, and Li-Cor.

Peptides include D and L forms, either purified or in a mixture of the two forms. Also contemplated by the present disclosure are peptides that compete with peptides of the invention for binding to HCC cells.

In some embodiments, a peptide of a reagent of the invention is presented in multimer form. Various scaffolds are known in the art upon which multiple peptides can be presented. In some embodiments, a peptide is presented in multimer form on a trilysine dendritic wedge. In some embodiments, a peptide is presented in dimer form using an aminohexanoic acid linker. Other scaffolds known in the art include, but are not limited to, other dendrimers and polymeric (e.g., PEG) scaffolds.

It will be understood that peptides and linkers of the invention optionally incorporate modifications known in the art and that the location and number of such modifications are varied to achieve an optimal effect in the peptide and/or linker analog.

In some embodiments, the compound is a peptide analog having a structure based on one of the peptides disclosed herein (the "parent peptide") but differs from the parent peptide in one or more respects. Accordingly, as appreciated by one of ordinary skill in the art, the teachings regarding the parent peptides provided herein may also be applicable to the peptide analogs.

In some embodiments, the peptide analog comprises the structure of a parent peptide, except that the peptide analog comprises one or more non-peptide bonds in place of peptide bond(s). In some embodiments, the peptide analog comprises in place of a peptide bond, an ester bond, an ether bond, a thioether bond, an amide bond, and the like. In some embodiments, the peptide analog is a depsipeptide comprising an ester linkage in place of a peptide bond.

In some embodiments, the peptide analog comprises the structure of a parent peptide described herein, except that the peptide analog comprises one or more amino acid substitutions, e.g., one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative ammo acid substitution may be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

In some aspects, the peptide analog comprises one or more synthetic amino acids, e.g., an amino acid non-native to a mammal. Synthetic amino acids include β-alanine β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethylcysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO$_2$)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2, 3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid.

In some embodiments, the peptide analog comprises one or more non-conservative amino acid substitutions and the peptide analog still functions to a similar extent, the same extent, or an improved extent as the parent peptide. In certain embodiments, the peptide analog comprising one or more non-conservative amino acid substitutions exhibits about the same or greater binding to HCC cells in comparison to the parent peptide.

In some embodiments, the peptide analog comprises one or more amino acid insertions or deletions, in comparison to the parent peptide described herein. In some embodiments, the peptide analog comprises an insertion of one or more amino acids in comparison to the parent peptide. In some embodiments, the peptide analog comprises a deletion of one or more amino acids in comparison to the parent peptide. In some embodiments, the peptide analog comprises an insertion of one or more amino acids at the N- or C-terminus in comparison to the parent peptide. In some embodiments, the peptide analog comprises a deletion of one or more amino acids at the N- or C-terminus in comparison to the parent peptide. In these embodiments, the peptide analog still exhibits about the same or greater binding to HCC cells in comparison to the parent peptide.

Detectable Markers

As used herein, a "detectable marker" is any label that can be used to identify the binding of a composition of the disclosure to HCC cells. Non-limiting examples of detectable markers are fluorophores, chemical or protein tags that enable the visualization of a polypeptide. Visualization in certain aspects is carried out with the naked eye, or a device (for example and without limitation, an endoscope) and may also involve an alternate light or energy source. As another example, nuclear imaging modalities such as PET/SPECT are contemplated.

Fluorophores, chemical and protein tags that are contemplated for use in the invention include, but are not limited to, FITC, Cy 5.5, Cy 7, Li-Cor, a radiolabel, biotin, luciferase, 1,8-ANS (1-Anilinonaphthalene-8-sulfonic acid), 1-Anilinonaphthalene-8-sulfonic acid (1,8-ANS), 5-(and-6)-Carboxy-2', 7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, C5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, eYFP (Enhanced Yellow Fluorescent Protein), FDA, FITC antibody conjugate pH 8.0, FlAsH, Fluo-3, Fluo-3 Ca2$^+$, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2$^+$, Fura Red, high Ca, Fura Red, low Ca, Fura-2 Ca2+, Fura-2, Fura-2, GFP (S65T), HcRed, Indo-1 Ca2$^+$, Indo-1, Ca free, Indo-1, Ca saturated, JC-1, JC-1 pH 8.2, Lissamine rhodamine, Lucifer Yellow, CH, Magnesium Green, Magnesium Green Mg2+, Magnesium Orange, Marina Blue, mBanana, mCherry, mHoneydew, mOrange, mPlum, mRFP, mStrawberry, mTangerine, NBD-X, NBD-X, MeOH, NeuroTrace 500/525, green fluorescent Nissl stain-RNA, Nile Blue, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, R-Phycoerythrin pH 7.5, ReAsH, Resorufin, Resorufin pH 9.0, Rhod-2, Rhod-2 Ca2$^+$, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodamine Green pH 7.0, Rhodol Green antibody conjugate pH 8.0, Sapphire, SBFI-Na$^+$, Sodium Green Na$^+$, Sulforhodamine 101, Tetramethylrhodamine antibody conjugate pH 8.0, Tetramethylrhodamine dextran pH 7.0, and Texas Red-X antibody conjugate pH 7.2.

Non-limiting examples of chemical tags contemplated by the invention include radiolabels. For example and without limitation, radiolabels that contemplated in the compositions and methods of the present disclosure include $^{11}$C, $^{13}$N, $^{15}$O, $^{18}$F, $^{32}$P, $^{52}$Fe, $^{62}$Cu, $^{64}$Cu, $^{67}$Ga, $^{68}$Ga, $^{86}$Y, $^{89}$Zr, $^{90}$Y, $^{94}$mTc, $^{94}$Tc, $^{95}$Tc, $^{99}$mTc, $^{103}$Pd, $^{105}$Rh, $^{109}$Pd, $^{111}$Ag, $^{111}$In, $^{123}$I, $^{124}$I, $^{125}$I, $^{131}$I, $^{140}$La, $^{149}$Pm, $^{153}$Sm, $^{154-159}$Gd, $^{165}$Dy, $^{166}$Dy, $^{166}$Dy, $^{169}$Yb, $^{175}$Yb, $^{175}$Lu, $^{177}$Lu, $^{186}$Re, $^{188}$Re, $^{192}$Ir, $^{198}$Au, $^{199}$Au, and $^{212}$Bi.

A worker of ordinary skill in the art will appreciate that there are many such detectable markers that can be used to visualize a cell, in vitro, in vivo or ex vivo.

Therapeutic Moieties

Therapeutic moieties contemplated by the invention include, but are not limited to polypeptides (including protein therapeutics) or peptides, small molecules, chemotherapeutic agents, or combinations thereof.

The term "small molecule", as used herein, refers to a chemical compound, for instance a peptidometic or oligonucleotide that may optionally be derivatized, or any other low molecular weight organic compound, either natural or synthetic.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

In some embodiments, the therapeutic moiety is a protein therapeutic. Protein therapeutics include, without limitation, cellular or circulating proteins as well as fragments and derivatives thereof. Still other therapeutic moieties include polynucleotides, including without limitation, protein coding polynucleotides, polynucleotides encoding regulatory polynucleotides, and/or polynucleotides which are regulatory in themselves. Optionally, the compositions comprise a combination of the compounds described herein.

In some embodiments, protein therapeutics include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Therapeutic moieties also include, in some embodiments, chemotherapeutic agents. A chemotherapeutic agent contemplated for use in a reagent of the invention includes, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Chemotherapeutic agents such as gefitinib, sorafenib and erlotinib are also specifically contemplated.

Therapeutic moieties also include micelles that, in turn, encapsulate another therapeutic moiety. In some embodiments, the micelles are polymeric micelles such as octadecyl lithocholate micelles. Peptides described herein are attached to polymeric micelles such as octadecyl lithocholate micelles described in Khondee et al., *J. Controlled Release*, 199: 114-121 (2015) and U.S. Provisional Patent Application No. 62/262,195. In some embodiments, the micelles encapsulate sorafenib. In some embodiments, the micelles are D-α tocopherol succinate micelles.

Dosages of the therapeutic moiety provided are administered as a dose measured in, for example, mg/kg. Contemplated mg/kg doses of the disclosed therapeutics include about 1 mg/kg to about 60 mg/kg. Specific ranges of doses in mg/kg include about 1 mg/kg to about 20 mg/kg, about 5 mg/kg to about 20 mg/kg, about 10 mg/kg to about 20 mg/kg, about 25 mg/kg to about 50 mg/kg, and about 30 mg/kg to about 60 mg/kg. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

"Effective amount" as used herein refers to an amount of a reagent of the invention sufficient to visualize the identified disease or condition, or to exhibit a detectable therapeutic or inhibitory effect. The effect is detected by, for example, an improvement in clinical condition or reduction in symptoms. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

Visualization of Reagents

Visualization of binding to HCC cells is by any means known to those of ordinary skill in the art. As discussed herein, visualization is, for example and without limitation, in vivo, in vitro, or in situ visualization.

In some embodiments where the detectable label is a radiolabel, the radiolabel is detected by nuclear imaging.

In some embodiments where the detectable label is a fluorophore, the fluorophore is detected by near infared (NIR) fluorescence imaging.

Some embodiments of methods of the invention involve the acquisition of a tissue sample from a patient. The tissue sample is selected from the group consisting of a tissue or organ of said patient.

Formulations

Compositions of the invention are formulated with pharmaceutically acceptable excipients such as carriers, solvents, stabilizers, adjuvants, diluents, etc., depending upon the particular mode of administration and dosage form. The compositions are generally formulated to achieve a physiologically compatible pH, and range from a pH of about 3 to a pH of about 11, about pH 3 to about pH 7, depending on the formulation and route of administration. In alternative embodiments, the pH is adjusted to a range from about pH 5.0 to about pH 8. In various aspects, the compositions comprise a therapeutically effective amount of at least one compound as described herein, together with one or more pharmaceutically acceptable excipients. Optionally, the compositions comprises a combination of the compounds described herein, or may include a second active ingredient useful in the treatment or prevention of bacterial growth (for example and without limitation, anti-bacterial or anti-microbial agents), or may include a combination of reagents of the invention.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

EXAMPLES

The invention will be more fully understood by reference to the following examples which detail exemplary embodiments of the invention.

Example 1

Expression of GPC3

Figures 1, 2:
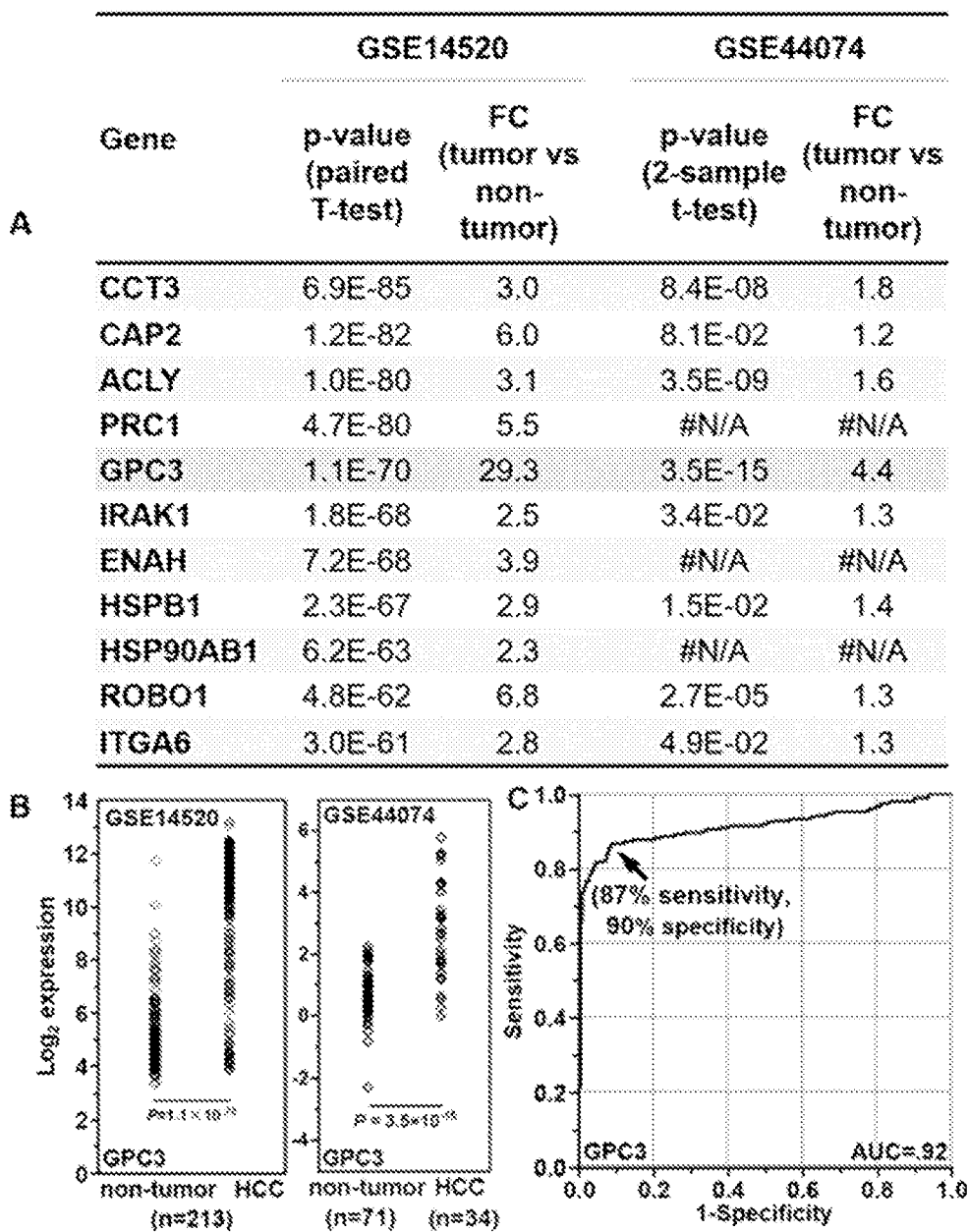
Figure 2:
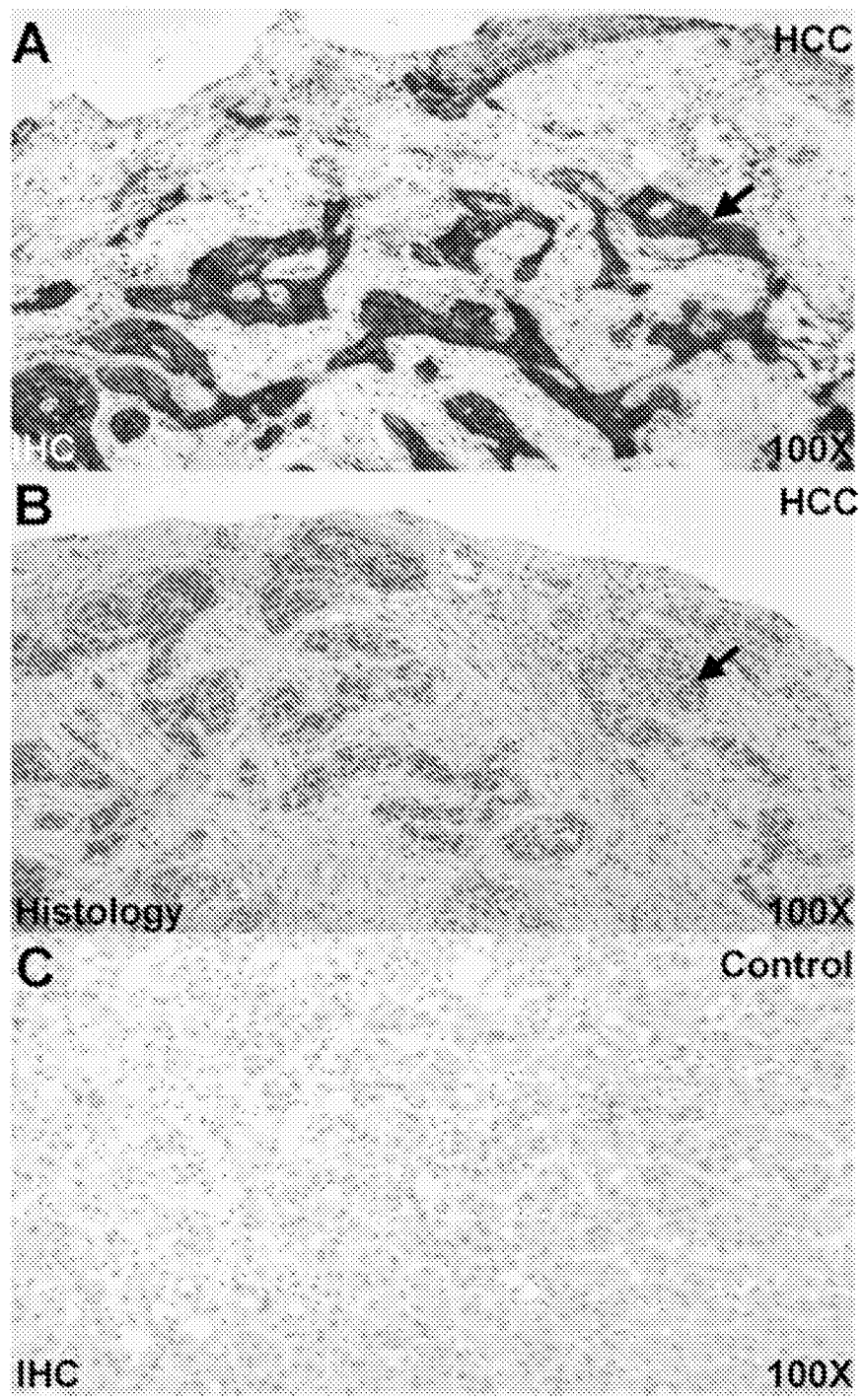

We identified GPC3 as a promising target for detecting and treating HCC using datasets GSE14520 [Roessler et al., Cancer Res, 70:10202-10212 (2010)] and GSE44074 [Ueda et al., Genomics,101:238-248 (2013)]. Expression levels of GPC3 showed large differences in P-value and average fold-change compared with non-tumor, FIG. 1-1A. Differences are reflected by the distribution of gene expression levels shown in $\log_2$, as shown for the dataset GSE14520 in FIG. 1-1B. FIG. 1-2B shows the same dataset GSE14520 as shown in FIG. 1-1B and shows the additional dataset GSE44074 (i.e. shows both datasets). The ROC curve for this data shows 89% sensitivity and 92% specificity with an area-under-the curve (AUC) of 0.92, FIG. 1-1C. These results show that GPC3 is a promising target for HCC. FIG. 1-2A shows the same data as shown in FIG. 1-1A, with additional analysis. FIG. 1-2C is similar to the data shown in FIG. 1-1C but represents data analysis from two the two different data sets (GSE14520 and GSE44074).

GPC3 overexpression was validated in HBV-derived HCC specimens from the bio-bank at the Peking University People's Hospital. n=25 formalin-fixed, paraffin-embedded tumors were evaluated, including n=23 HBV-related HCC, n=1 liver metastasis (breast cancer), and n=1 focal nodular hyperplasia. Sections were processed using standard methods, including deparaffinization, rehydration, and antigen unmasking. Staining for GPC3 using an anti-GPC3 antibody was found to be strong for n=16 and moderate for n=6 specimens in regions of tumor. A representative specimen shows patches of strong staining in areas of HCC tumor (arrow) surrounded by relatively unstained adjacent regions of cirrhosis, FIG. 2A. Histology (H&E) from a serial section shows HCC, FIG. 2B. Negative staining was found in non-tumor (control), FIG. 2C.

Example 2

Peptides Specific for GPC3

A panel of candidate peptides that are specific to GPC3 was identified using phage display technology. Peptide selection was performed using a library of M13 bacteriophage that express ~$10^9$ unique clones of each individual sequence [Zhou et al., Clin Transl Gastroenterol, 6:e101 (2015); Joshi et al., Bioconjug Chem, 27:481-494 (2016); Rabinsky et al., Cell Mol Gastroenterol Hepatol, 2:222-237 (2016)]. The library was biopanned against purified recombinant GPC3 core protein immobilized in a 6-well plate. Four rounds of biopanning were performed using decreasing quantity (100, 80, 60, and 40 µg) of GPC3 core protein in successive rounds to increase binding specificity. The bound phages were eluted, amplified, precipitated and tittered using standard protocols, and the enriched clones from the candidate pool were sequenced to identify the lead candidates: ALLANHEELF (SEQ ID NO: 2), GLHTSATNLYLH (SEQ ID NO: 3), SGVYKVAYDWQH (SEQ ID NO: 4) and VGVESCASRCNN (SEQ ID NO: 5). The peptide ALLANHEELF (SEQ ID NO: 2) showed the highest level of enrichment, and was labeled with the water soluble dye sulfo-Cy5.5-N-hydroxysuccinimide ester (Lumiprobe LLC) via a GGGSK (SEQ ID NO: 7) linker using standard Fmoc-mediated solid-phase synthesis.

A structural model was used to optimize the sequence of the ALL peptide for maximum binding affinity to GPC3. See, Macindoe et al., Nucleic Acids Research, 38(S2): W445-W449 (2010). Peptide alignment to the target was evaluated by rotating the receptor and ligand about their centers of mass over a full range of intermolecular distances and rotational angles [Svensson et al., J Biol Chem, 287: 14040-14051 (2012)]. Several mutations of the lead peptide sequence were compared to achieve the lowest docking energy, aiming to achieve a value of $E_t$<-600. Scrambled peptides were also developed using the structural model for use as controls.

Figure 3:
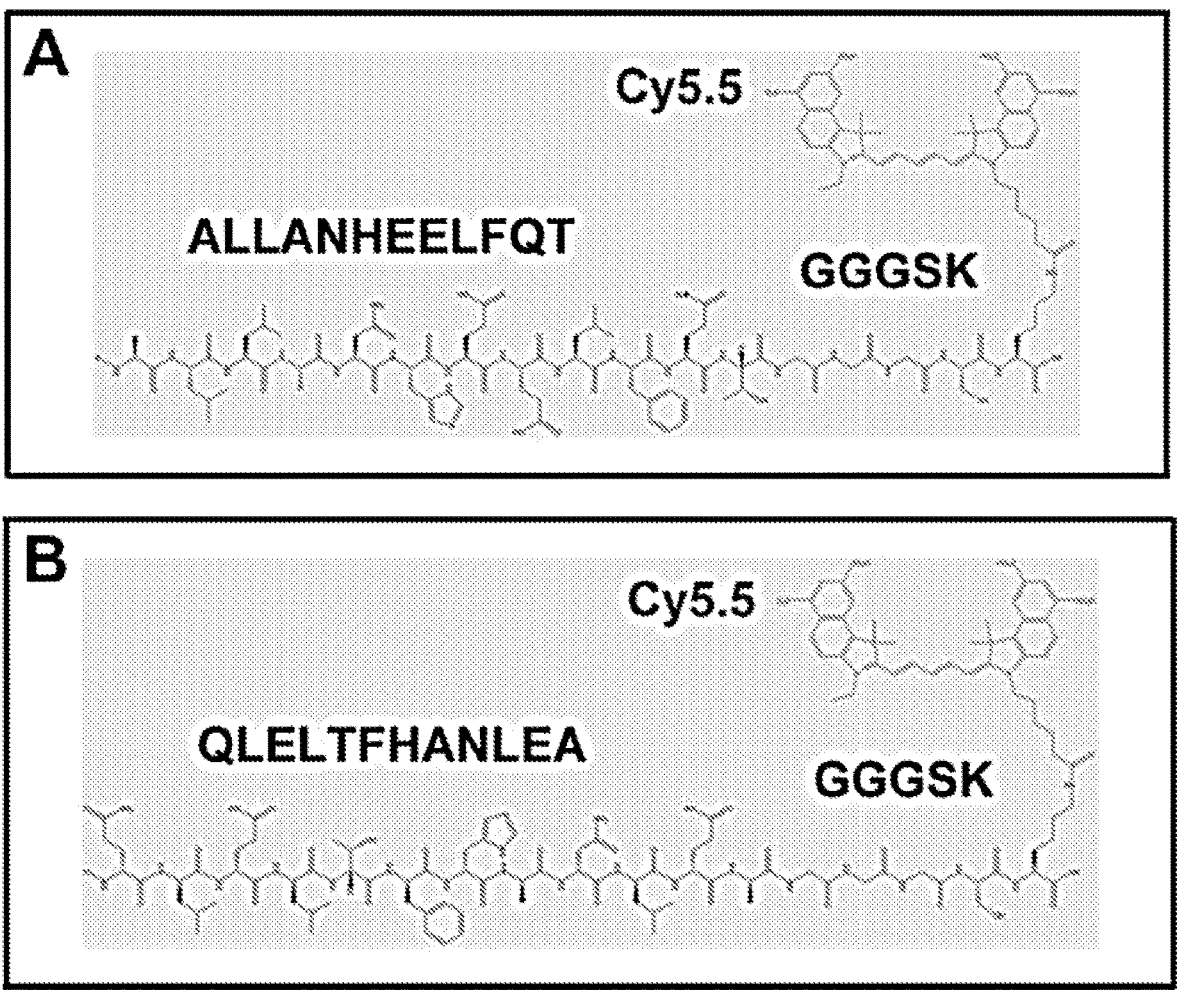
FIGS. 3A-B show chemical structures of peptide reagents described herein. A) ALLANHEELFQT peptide found to be highly specific for GPC3 with GGGSK linker and Cy5.5 fluorophore, hereafter ALL*-Cy5.5. B) Scrambled control peptide QLELTFHANLEA, hereafter QLE*-Cy5.5.

The optimized GPC3 and scrambled (control) peptides were attached to Cy5.5 via a GGGSK (SEQ ID NO: 7) linker on the C-terminus to prevent steric hindrance. FIGS. 3A and B respectively show the biochemical configurations for the optimized lead candidate peptide ALLANHEELFQT (SEQ ID NO: 1) (referred to as ALL* peptide herein) and a scrambled (control) peptide QLELTFHANLEA (SEQ ID NO: 6) (referred to as QLE* peptide herein) each labeled with sulfo-Cy5.5-N-hydroxysuccinimide ester (Lumiprobe LLC) via a GGGSK (SEQ ID NO: 7) linker. The labeled lead candidate peptide reagent was named ALL*-Cy5.5.

Figure 4:
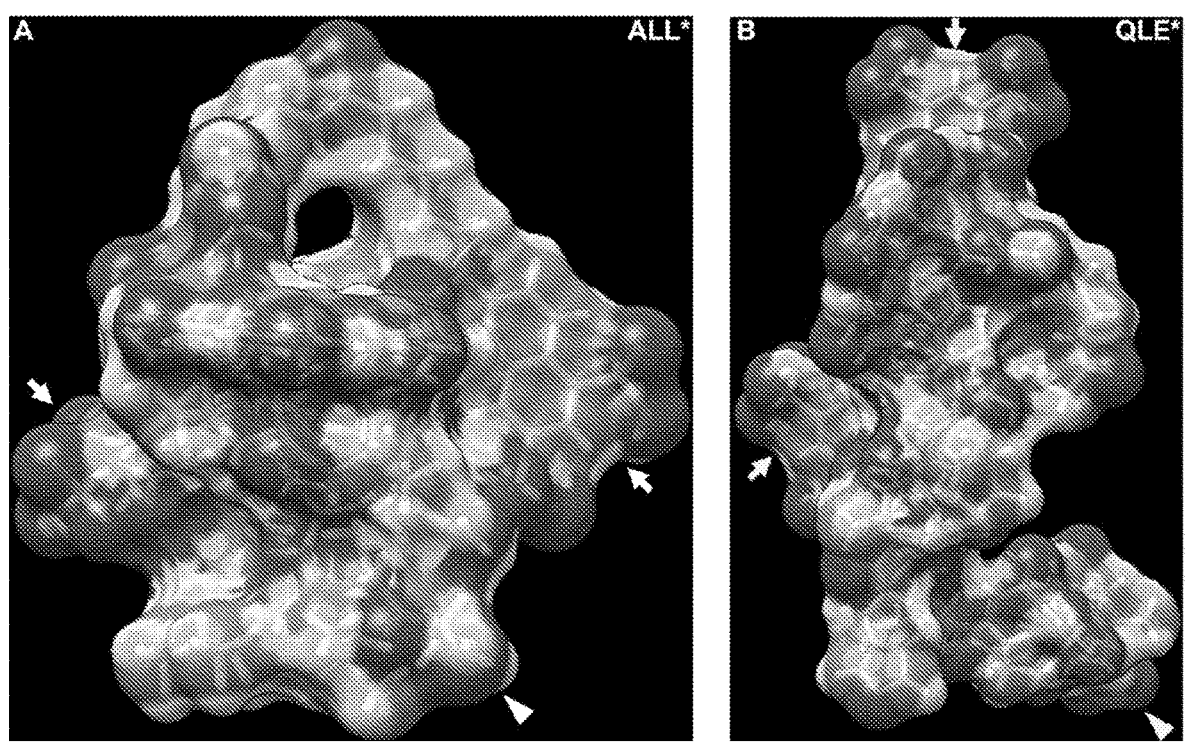
FIGS. 4A-B show 3D structures of labeled targeting and scrambled control peptides. Structural differences were observed between the A) lead candidate peptide ALL* specific for GPC3 and the B) scrambled control peptide QLE*. The near-infrared fluorophore Cy5.5 dye was labeled on C-terminal of each 12-mer peptide and the sulfonated benzo-fused indolenine rings are marked with arrows. The N-terminals of peptides where the sequence begins are denoted with arrow heads. Both the overall shapes and local chemical environments are different in the two probes. Molecular graphics and analyses of the peptides were performed with the UCSF Chimera package (v. 1.10.2, University of California, San Francisco).
Figure 5:
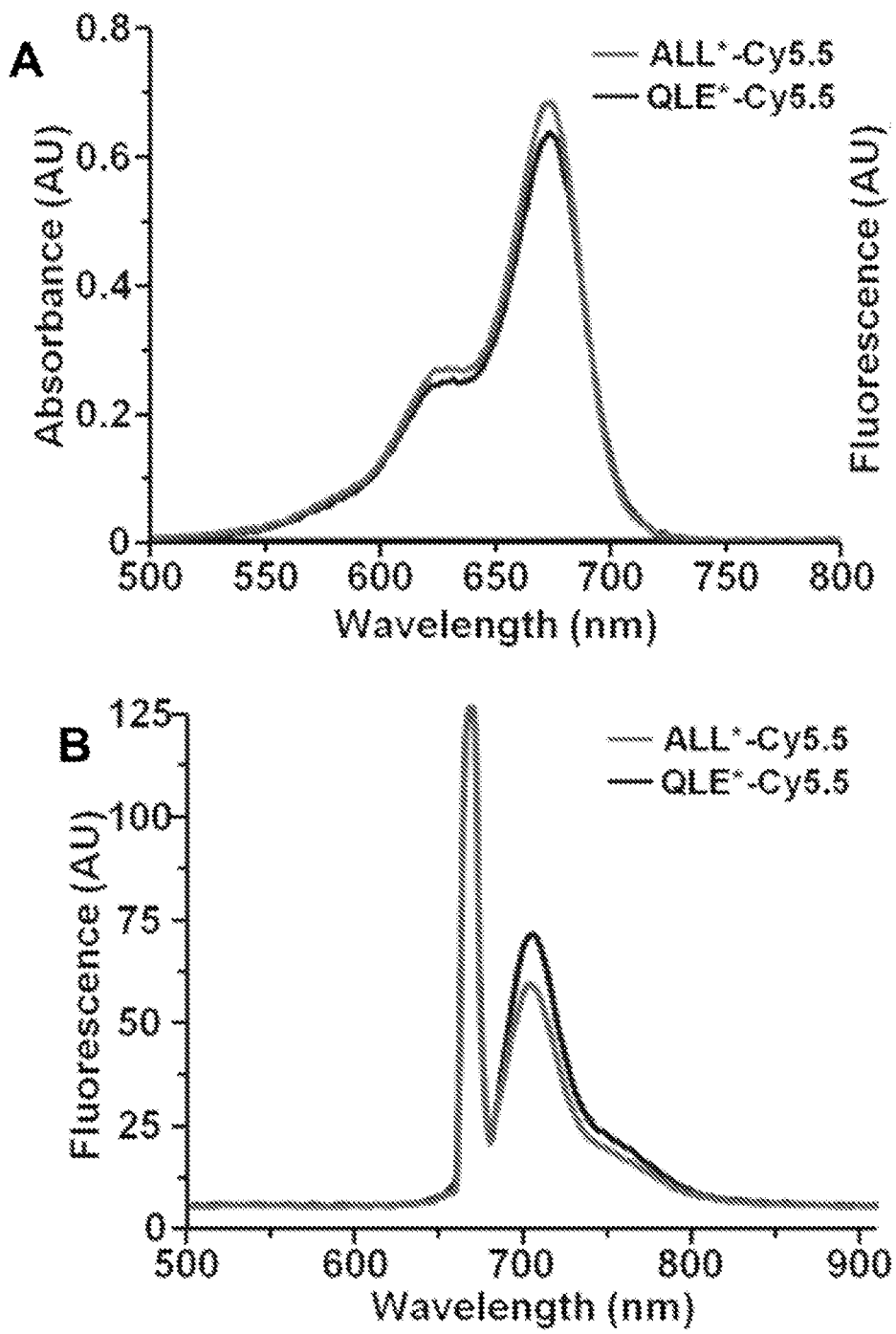
FIGS. 5A-B show absorbance and fluorescence of Cy5.5-labeled GPC3 peptides A) Absorbance spectra of Cy5.5-labeled peptides shows peak at $\lambda ex=677$ nm. B) Maximum fluorescence emission is seen at $\lambda em=708$ nm for both peptides.

Structural differences between the lead candidate peptide reagent specific for GPC3 and the scrambled control peptide can be seen in FIGS. 4A and B, respectively. The sulfonated benzo-fused indolenine rings are marked with arrows. The N-termini of peptides are denoted with arrow heads. Both the overall shapes and local chemical environments are different between the two peptides. The absorbance spectra of either peptide at 10 µM in PBS show a maximum at $\lambda_{ex}$=677 nm, FIG. 5A. The fluorescence emission spectra of either peptide with $\lambda_{ex}$=671 nm excitation (using a diode-pumped solid-state laser with 671 nm output wavelength) revealed a peak emission at $\lambda_{em}$=708 nm, FIG. 5B.

Example 3 siRNA Knockdown of GPC3

Figures 1, 6:
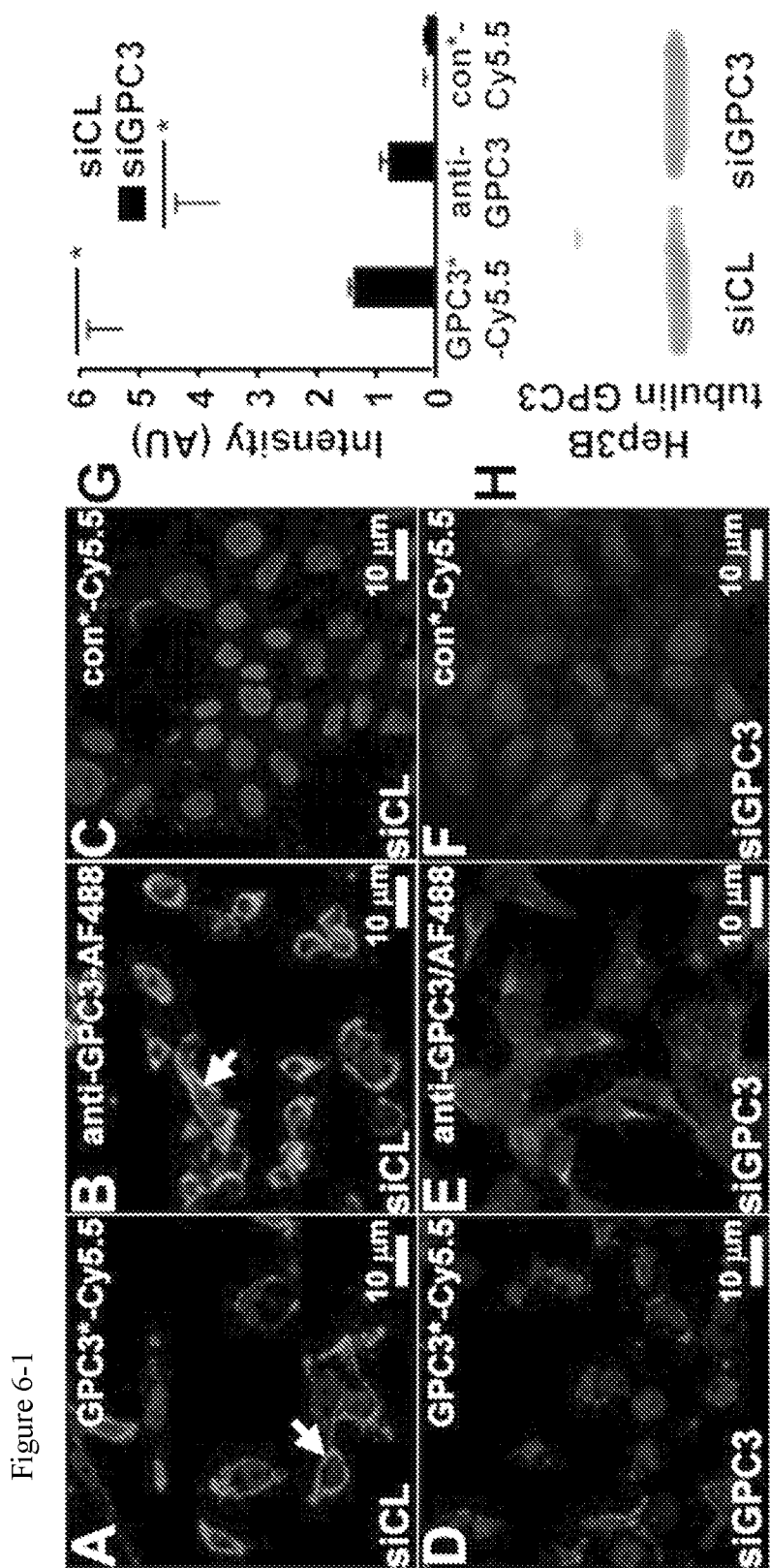
Figures 2, 6:
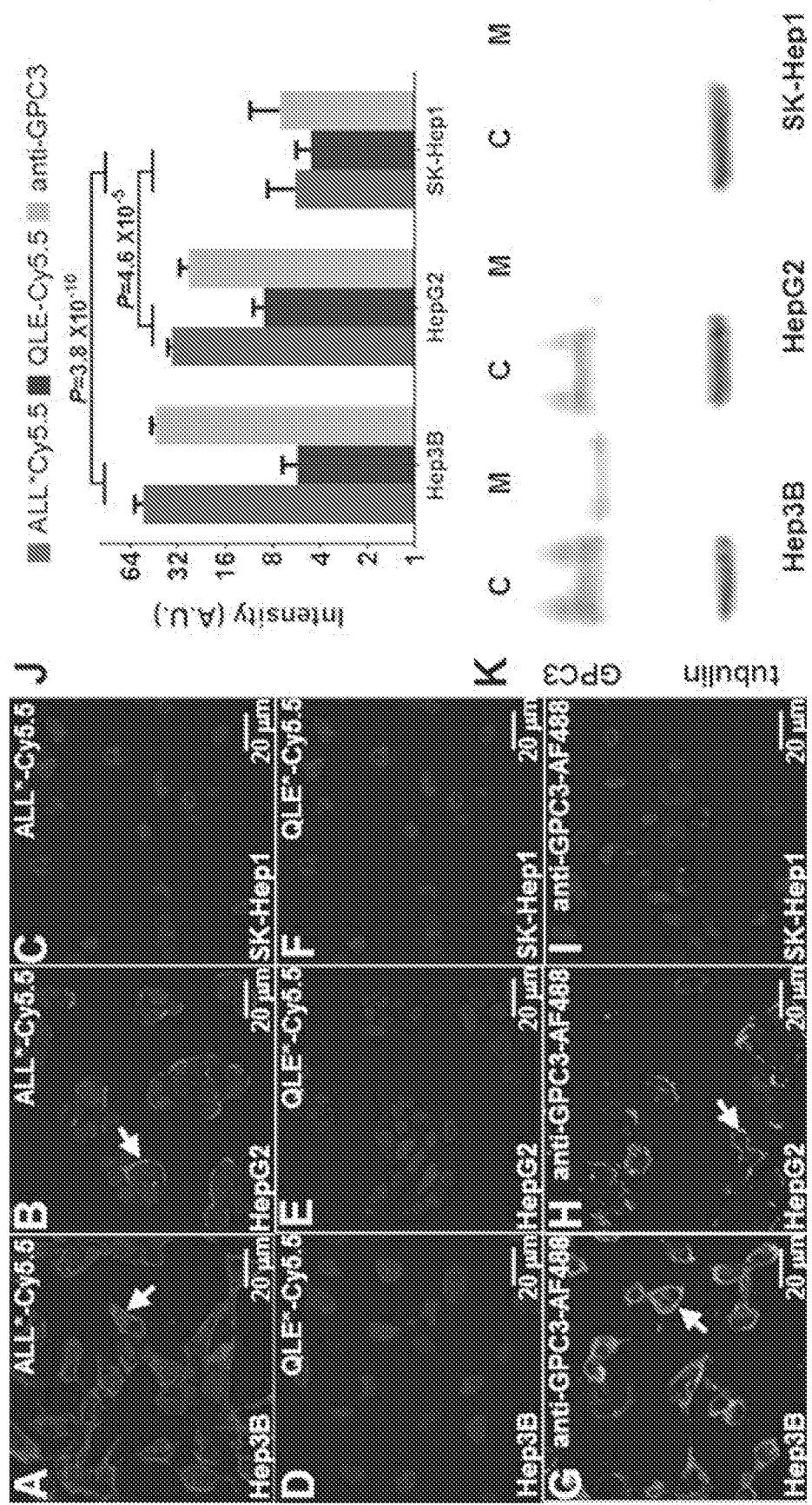
Figures 2, 6:
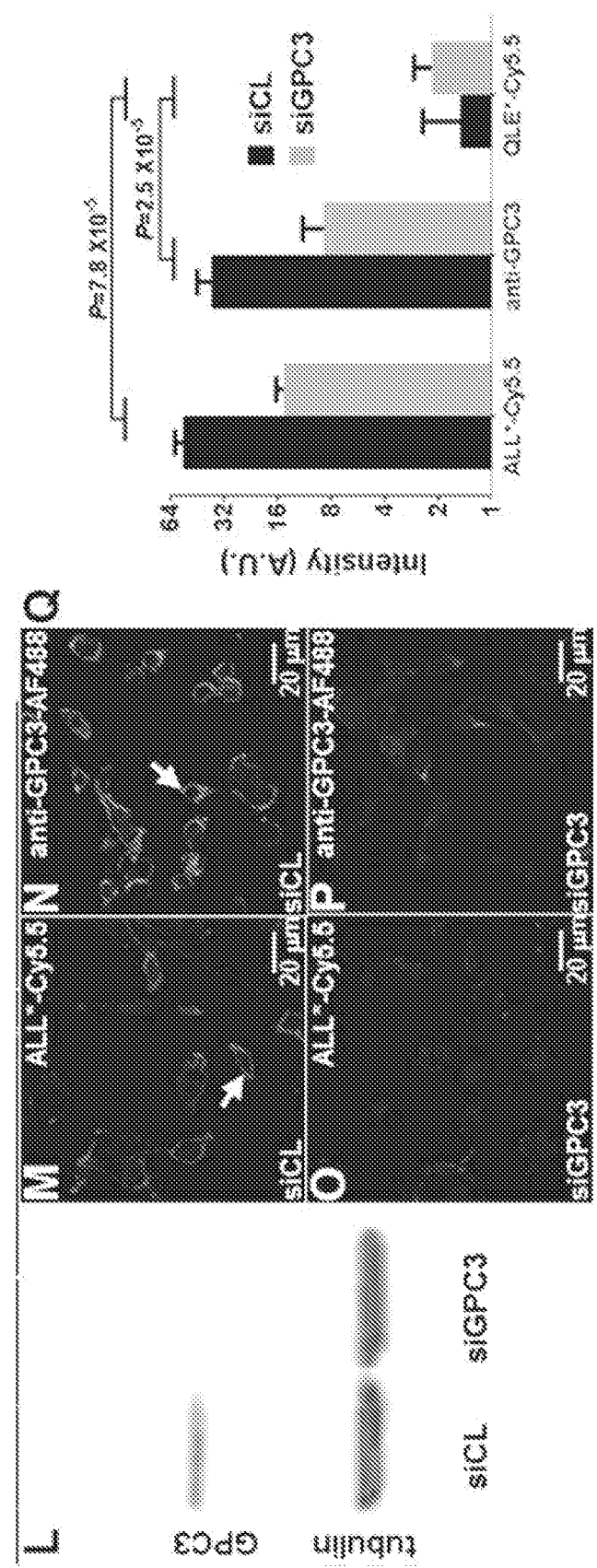

The specificity of lead candidate peptide reagent binding was validated by siRNA knockdown of GPC3 in human HCC cells. The cells were transfected with siRNA to knockdown cell surface expression of GPC3. On confocal microscopy, FIG. 6-1A shows ALL*-Cy5.5 peptide reagent and FIG. 6-1B shows AF488-labeled anti-GPC3 antibody with strong binding to the cell surface (arrows) of Hep3B cells. These cells were transfected with non-targeting siRNA (siCL) for use as control. FIG. 6-1C,F shows minimal binding of the scrambled (control) peptide QLE*-Cy5.5 to the same cells. FIG. 6-1D,E show ~4-fold reduction in fluorescence intensity with both the peptide reagent and anti-GPC3 antibody, respectively, for Hep3B cells transfected with siRNA (siGPC3) to knock down GPC3 expression. FIG. 6-1G shows the results of measurements of fluorescence intensity from images collected in triplicate. FIG. 6-1H shows Western blot of GPC3 expression in Hep3B cells. FIG. 6-2L shows the same result as original FIG. 6-1H. FIG. 6-2M, N, O and P show the same result as original FIG. 6-1A, B, D and E.

On confocal microscopy, it was shown that ALL*-Cy5.5 binds to the surface (arrows) of cells with different levels of GPC3 expression. Strong fluorescence intensity was observed from binding by ALL*-Cy5.5 to the surface (arrows) of Hep3B cells and a slight reduction in signal to HepG2 cells, FIG. 6-2A,B. Little signal was seen for SK-Hep1 cells, FIG. 6-2C. Minimal signal was seen with the scrambled control QLE*-Cy5.5 for all cells, FIG. 6-2D-F. We used AF488-labeled anti-GPC3 antibody as a positive control, and observed a steady decline in intensity with ALL*-Cy5.5 to the 3 cells, FIG. 6-2G-I. Quantified results are shown, FIG. 6-2J. Western blot shows difference in expression level of GPC3 in the cytoplasm (C) and on the membranes (M) for the cells studied, FIG. 6-2K. GPC3 is highly overexpressed in Hep3B cell cytosol and membrane while moderately expressed in HepG2 cells. No GPC3 expression is observed in SK-Hep1 cells. Tubulin serves as loading control for either cytosol or membrane fractions loaded. The fluorescence intensity was found to be reduced with peptide by 27% in GPC3 knockdown cells and with antibody by 23%, FIG. 6-2Q.

Example 4

Competition for Peptide Binding

Figure 7:
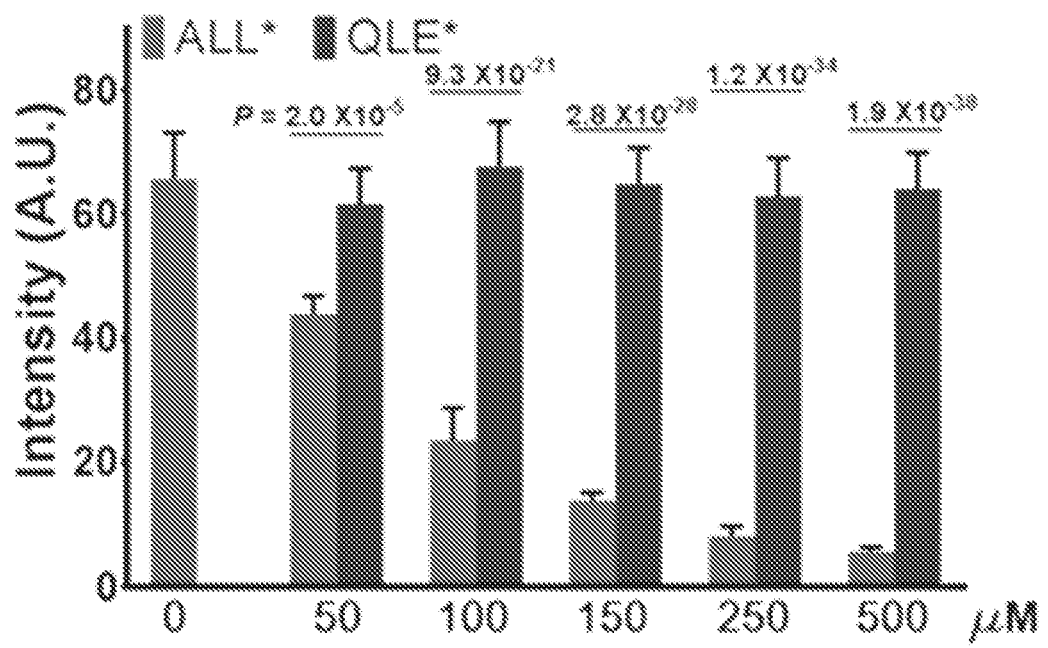
FIG. 7 shows validation of specific peptide binding on competition. Fluorescence intensities (mean±SD) show a significant decrease in ALL*-Cy5.5 binding to Hep3B cells with addition of unlabeled ALL* at concentrations of 50 μM and higher. P values by ANOVA model with terms for 11 means are shown above each result. Addition of unlabeled QLE* (scrambled control) peptide showed no change. Each result was an average of 6 independent measurements.

The specificity of peptide reagent binding was also validated by competition assay. Hep3B cells were grown on cover glass and incubated first with unlabeled peptides over a range of concentrations (0-500 µM), and then with ALL*-Cy5.5 peptide. The fluorescence intensities were measured using confocal microscopy. FIG. 7 shows a dose-dependent decrease in fluorescence intensity as increasing concentrations of unlabeled ALL* peptide were added to compete with binding by ALL*-Cy5.5 peptide reagent to Hep3B cells. Differences in fluorescence intensity between the ALL*-Cy5.5 peptide reagent and control are significant at concentrations of 50 µM and greater.

Example 5

Characterization of Peptide Binding Affinity

The apparent dissociation constant (kd) was measured for the optimized GPC3 peptide to Hep3B cells to provide an assessment of peptide binding affinity. The ALL*-Cy5.5 peptide reagent was serially diluted in PBS at concentrations ranging from 0 to 200 nM in 25 nM increments and incubated with Hep3B cells. The mean fluorescence intensities was measured on flow cytometry. The equilibrium dissociation constant $k_d=1/k_a$ was calculated by performing a least squares fit of the data to the non-linear equation $I=(I_0+I_{max}k_a[X])/(I_0+k_a[X])$. $I_0$ and $I_{max}$ are the initial and maximum fluorescence intensities, corresponding to no peptide and at saturation, respectively, and [X] represents the concentration of the bound peptide. FIG. 8A shows a $k_d=71$ nM for ALL*-Cy5.5.

The apparent association time constant (k) was also measured for the optimized GPC3 peptide to provide an assessment of how rapidly the peptide binds. The ALL*-Cy5.5 peptide reagent was incubated with Hep3B cells over time intervals ranging from 0 to 40 min. Fluorescence intensities were measured on flow cytometry. The median fluorescence intensity (y) was ratioed with that of Hep3B cells without addition of peptide reagent at different time points (t). The rate constant k was calculated by fitting the data to a first order kinetics model, $y(t)=I_{max}[1-\exp^{(-kt)}]$, where $I_{max}$=maximum value.[46] FIG. 8B shows $k=0.11$ min$^{-1}$ for ALL*-Cy5.5 peptide reagent.

Example 6

In Vivo Whole Body Fluorescent Imaging

Figure 9:
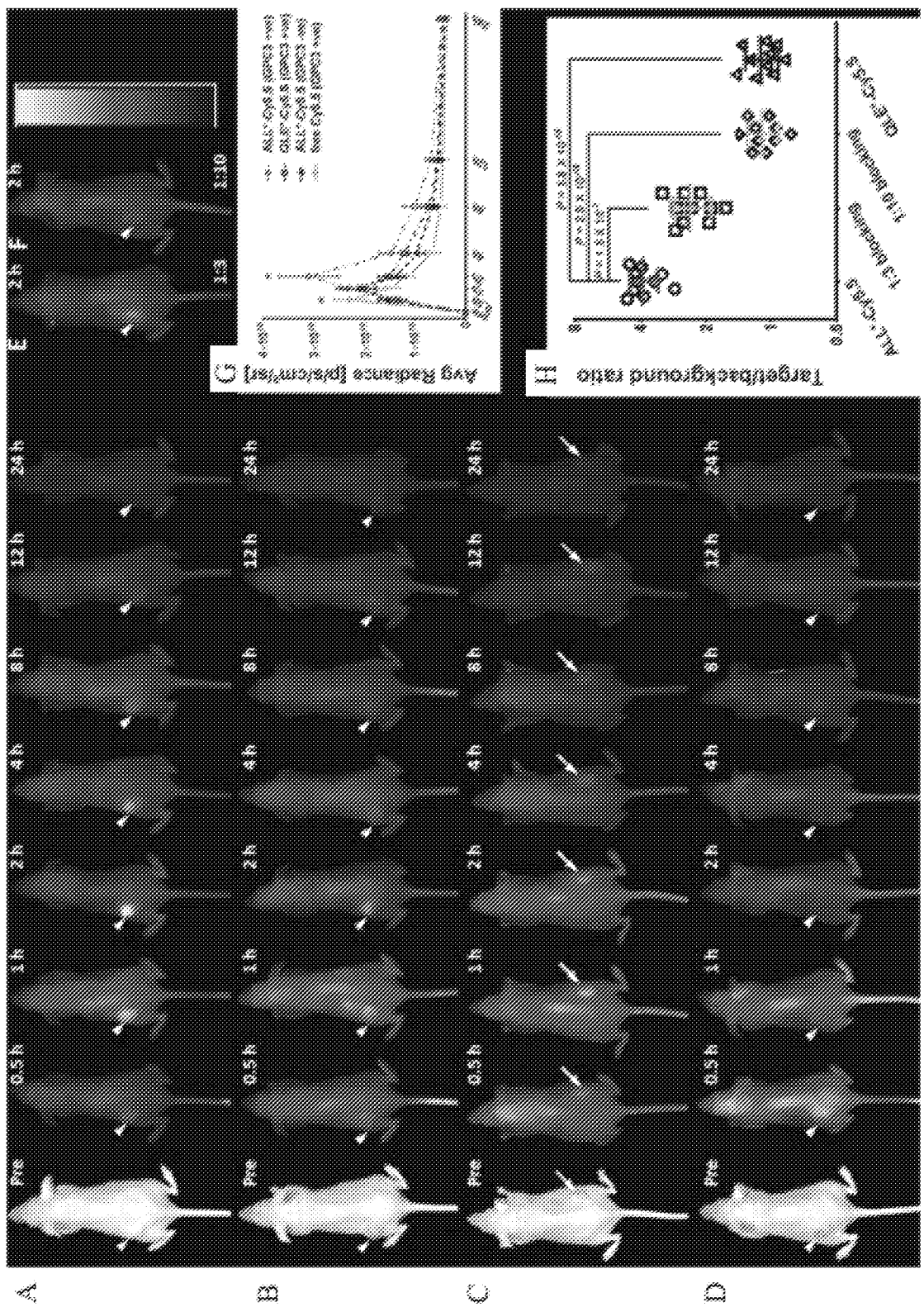
FIGS. 9A-H show pharmacokinetics of NIR dye labeled peptides in mice bearing HCC xenograft tumor in vivo. A) Representative whole-body images were taken prior to injection and over the time course of 0.5~24 hours post injection. Peak uptake in GPC3 positive tumor (from Hep3B cells, arrowheads) was observed at 2 hours after i.v. injection of ALL*-Cy5.5. B) Same dose of scrambled peptide QLE*-Cy5.5 was injected in mice bearing GPC3 positive tumor (arrowheads). C) ALL*-Cy5.5 was injected in mice bearing GPC3 negative tumor (from SK-Hep1 cells, arrows). D) Whole-body time course images of mice with GPC3 positive tumor (arrowheads) injected with unlabeled Cy5.5 dye alone. E,F) Reduction of signal from tumor in dose dependent manner was observed when unlabeled ALL* peptide at three-fold and ten-fold doses of the labeled peptide was injected respectively prior to ALL*-Cy5.5 injection in GPC3 positive tumor (arrowheads). G) Quantitative analysis of log-transformed data showed the mean signal from ALL*-Cy5.5 to be significantly higher than that of scrambled control peptide, targeting peptide in absence of target expression and free dye alone at 2 hours post injection ($P=4.3\times10^{-9}$, $1.7\times10^{-10}$ and $5.6\times10^{-14}$ respectively). Signal from free Cy5.5 dye peaked at 0.5 hour post injection and was significantly higher than labeled peptides ($P=2.7\times10^{-6}$, $1.2\times10^{-5}$ and $4.7\times10^{-4}$ vs ALL, QLE, and GPC3-ve respectively). H) Mean±SD target-to-background (T/B) ratio of ALL*-Cy5.5 at 2 hours was 3.91±0.58 versus 1.12±0.19 for QLE*-Cy5.5, $P=3.8\times10^{-18}$. Blocking with 3-fold and 10-fold unlabeled targeting peptide doses reduced T/B ratio by 1.65 and 3.56 folds, $P=1.3\times10^{-7}$ and $2.5\times10^{-18}$ respectively.

Mice bearing HCC xenograft tumor (arrowheads) were i.v. injected with 250 µL of 300 µM near NIR GPC3 targeting peptide ALL*-Cy5.5, scrambled control peptide QLE*-Cy5.5 and unlabeled Cy5.5 free dye alone. ALL*-Cy5.5 was also injected in mice bearing GPC3 negative tumor (from SK Hep-1 cells, arrows) as control of EPR effect. Pre-injection imaging confirmed no autofluorescence was present. NIR images were taken over the time course of 0.5~24 hours post injection, FIG. 9A-D. A reduction of signal from tumor in dose dependent manner was observed when unlabeled ALL* peptide at three-fold and ten-fold doses of the labeled peptide was injected respectively prior to ALL*-Cy5.5 injection in GPC3 positive tumor (arrowheads), FIG. 9E-F. Quantitative analysis of log-transformed data shows the mean signal from ALL*-Cy5.5 to be significantly higher than that of scrambled control peptide targeting peptide in absence of target expression and free dye alone at 2 hours post injection (P=4.3×10$^{-9}$, 1.7×10$^{-10}$ and 5.6×10$^{-14}$ respectively). Signal from free Cy5.5 dye alone was non-specific to tumor site, which peaked at 0.5 hour post injection and was significantly higher than labeled peptides (P=2.7×10$^{-6}$, 1.2×10$^{-5}$ and 4.7×10 vs ALL, QLE, and GPC3-ve respectively). FIG. 9G. Mean±SD target-to-background (T/B) ratio of ALL*-Cy5.5 at 2 hours was 3.91±0.58 versus 1.12±0.19 for QLE*-Cy5.5, P=3.8×10$^{-18}$. Blocking with 3-fold and 10-fold unlabeled targeting peptide doses reduced T/B ratio by 1.65 and 3.56 folds, P=1.3×10$^{-7}$ and 2.5×10$^{-18}$ respectively, FIG. 9H.

Example 7

Biodistribution of Peptide in Organs

Figure 10:
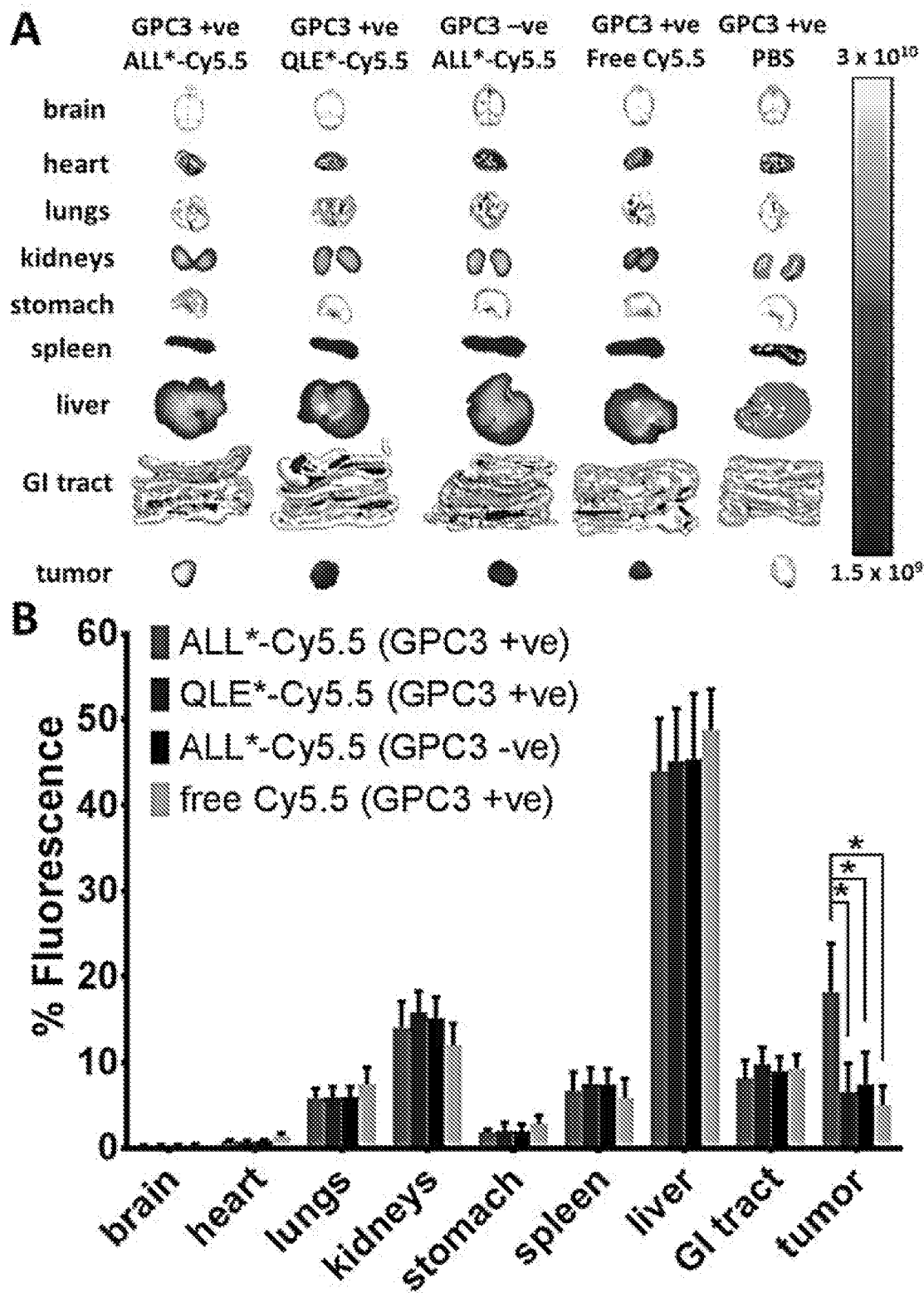
FIGS. 10A-B show biodistribution of the GPC3 peptide. A) Representative fluorescence images of excised organs 2 hours following intravenous injection of ALL*-Cy5.5, scrambled peptide QLE*-Cy5.5, free Cy5.5 dye, and PBS on GPC3 positive tumor bearing mice. In addition, ALL*-Cy5.5 was also injected in GPC3 negative tumor bearing mice as control (3rd column). B) Quantification of fluorescent signals in each organ. Signal in the tumor was significantly higher in ALL*-Cy5.5 injected mice than the scrambled control probe, targeting probe on GPC3 negative tumor, or free Cy5.5 dye ($P=2.6\times10-4$, $5.5\times10-4$ and $7.4\times10-5$ respectively, n=5), by ANOVAs for each tissue.

To assess the biodistribution of peptide probe, mice (n=5) were sacrificed 2 hours after injection of 250 µL of 300 µM ALL*-Cy5.5 using a fluorescence imaging system (IVIS Spectrum, PerkinElmer, Mass.). The organs were harvested and imaged ex vivo. Mice injected with scrambled control peptide, QLE*-Cy5.5 and free dye Cy5.5 were imaged with the same filters and exposure time. Absence of auto fluorescence was confirmed in PBS injected mice. The amount of fluorescent signal in each organ was quantified as a percentage of total fluorescence signal (p/s) in each mouse. Ex vivo fluorescence images taken of internal organs as well as resected tumor 2 hours post injection of probes are shown in FIG. 10A. Free Cy5.5 dye and Cy5.5 labeled targeting and scrambled peptides accumulated most in the liver and kidneys of mice, followed by GI tract and spleen. Much higher targeting peptide accumulation was observed in tumor than all other groups. Minimal accumulation was observed in brain, heart and stomach. No fluorescent signal was observed in negative control group injected with same volume of PBS. Signal in the tumor was significantly higher in ALL*-Cy5.5 injected mice than the scrambled control probe, targeting probe on GPC3 negative tumor, or free Cy5.5 dye ($P=2.6\times10^4$, $5.5\times10^{-4}$ 3 and $7.4\times10^{-5}$ respectively, n=5), by ANOVAs for each tissue, FIG. 10B.

Example 8

Peptide Binding to HCC Xenograft Tumor Cells

Human HCC cells Hep3B and SK-Hep1 were cultured in Eagle's Minimum Essential Medium (EMEM) at 37° C. in 5% CO2, and supplemented with 10% fetal bovine serum (FBS) and 1% penicillin/streptomycin. Western blotting was performed to validate expression level of GPC3. Cells were diluted in growth factor reduced (GFR) Matrigel Matrix (Corning), and injected into one flank of female (to avoid male dominance within a cage) nude athymic mice (nu/nu, Jackson Laboratory) at 4 to 6 weeks of age with weight between 20 to 25 grams. ~$5\times10^6$ cells were implanted per mouse.

A standard surgical laparoscope (#49003 AA, HOPKINS® II Straight Forward Telescope 0°, Karl Storz) that is ~10 mm in diameter and has a 31 cm length rigid sheath was adapted to collect reflectance and fluorescence concurrently. Nude mice with human HCC xenograft 2 weeks post implantation were tail vein injected with 200 µL 300 µM GPC3 peptide ALL*-Cy5.5. During imaging, the mice were anesthetized with inhaled isoflurane. We first used laparoscope with white light illumination to exam the xenograft. Laparoscopic images were taken two hours post injection in both fluorescence and reflection mode simultaneously with excitation solid state diode laser (660-S, Toptica Photonics) to deliver excitation at $\lambda_{ex}=660$ nm into the fiber optic light guide. Images were collected at 5 frames/sec with a laser power of 1.2 mW. Hoechst 33342 (H1399, Life Technologies) at a dose of 10 mg/kg diluted in 200 µL of PBS was delivered intravenously via a tail vein injection to stain the cell nuclei 30 minutes before sacrificing the mouse. Xenograft tumors were resected and confocal fluorescence images were collected with Cy5.5 and DAPI filters 50 µm beneath the surface using a confocal microscope (Leica SPSX Upright 2-Photon Confocal Microscope). Following imaging, resected xenografts were fixed and formalin embedded for immunohistochemistry and H&E staining as described previously.

Fluorescence images of mouse HCC xenograft taken at 2 hrs post peptide injection were registered with corresponding reflectance images taken simultaneously. The fluorescence intensity of each pixel in the image was divided by intensity of corresponding pixel in the reflectance image in order to account for the difference in distance between each pixel and the laser source. A heat map image was generated from the resulting ratios at each pixel. Image segmentation was performed automatically by custom Matlab (Mathworks) software program using Ostu's Method [Otsu, Automatica, 11(285-296): 23-27 (1975)]. Target to background ratio of each processed image was calculated by dividing the average intensity of pixels inside the segmented tumor and that of those within 30 pixels outside of segmentation outline.

Figures 1, 11:
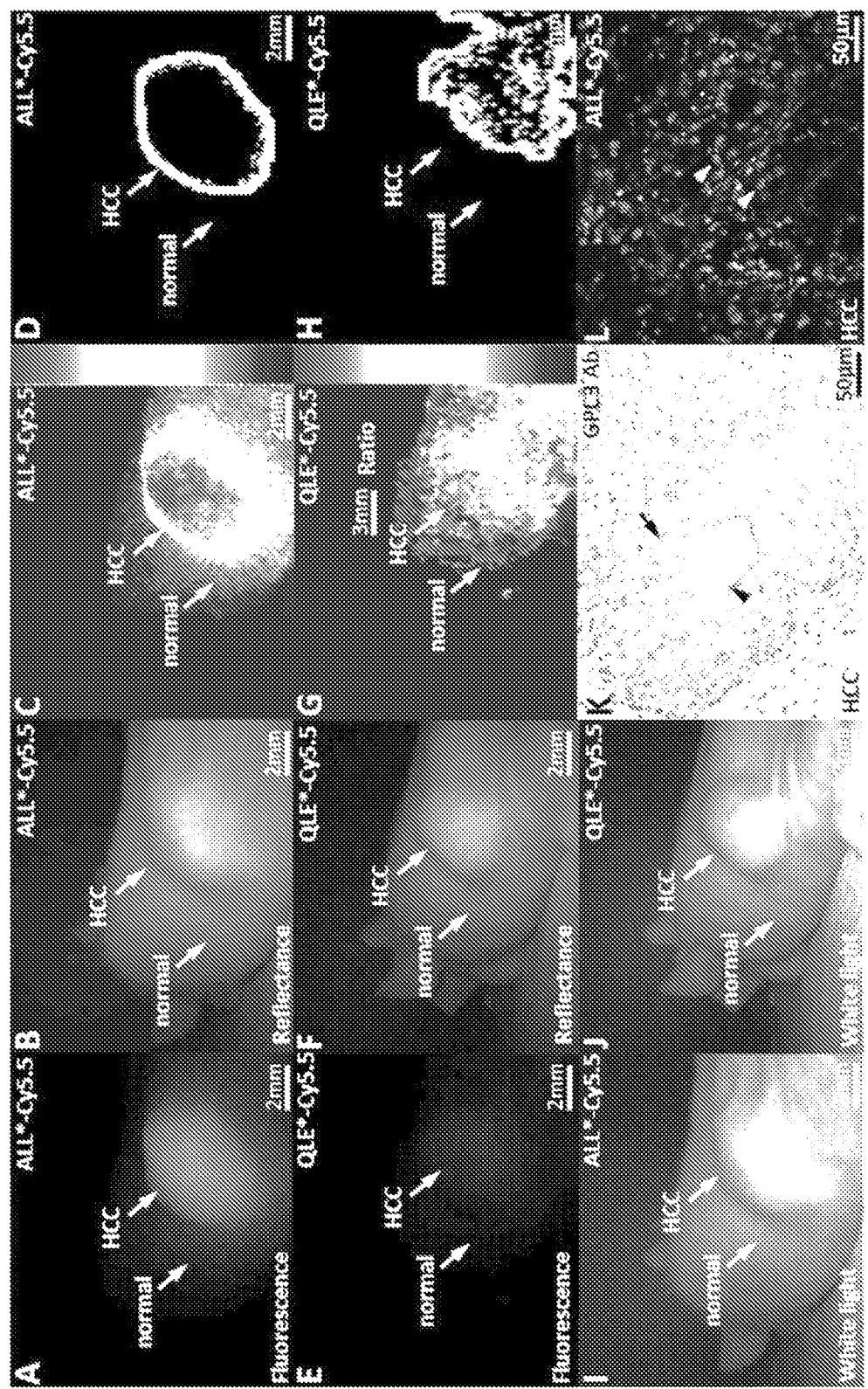
Figures 2, 11:
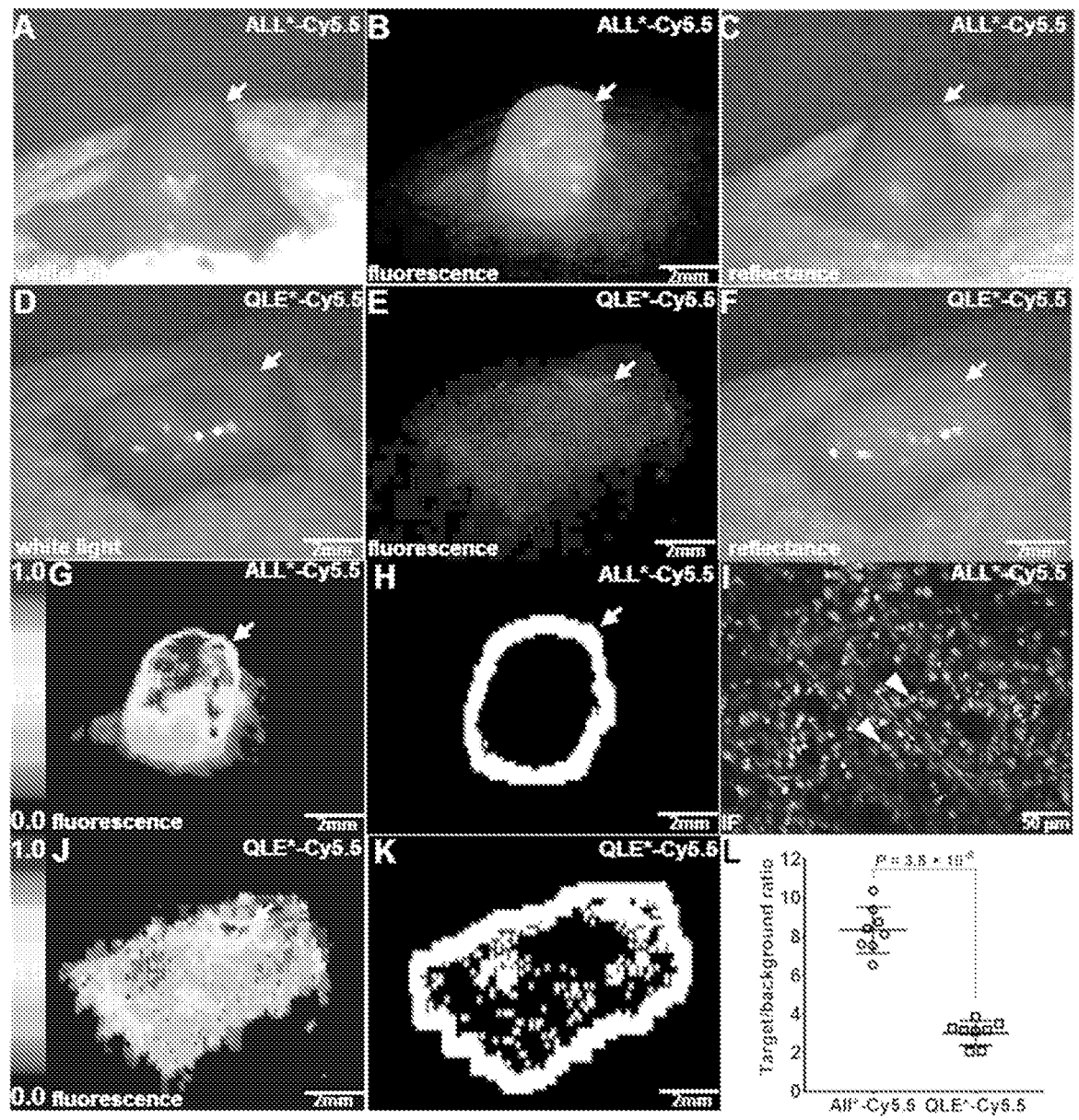

Fluorescence reflectance images, FIG. 11-1A, B, were collected with the NIR laparoscope 2 hours after intravenous injection of the GPC3-targeting peptide, QRH*-Cy5.5, in Hep3B xenograft bearing mice. Heat map digital image that rectifies imaging distance was generated by taking the ratio between corresponding fluorescence and reflectance images pixel by pixel, FIG. 11-1C. Region of interest (ROI) was segmented by automatic imaging processing from ratio image following Otsu's method, FIG. 11-1E. The same set of images were collected with scrambled peptide PEH*-Cy5.5 in a different tumor bearing mouse, FIG. 11-1E-H. White light images were collected for mouse injected with targeting peptide ALL*-Cy5.5, FIG. 11-1L, and scrambled peptide PEH*-Cy5.5, FIG. 11-1J. On immunohistochemistry, anti-GPC3 antibody stained strongly on cellular membrane (arrow) of tumor cells surrounding infiltrating blood vessel (arrow head) in resected HCC tumor xenograft, FIG. 11-1K. On confocal fluorescence microscopy, intense staining of ALL*-Cy5.5 to surface of Hep3B human HCC cells (arrow heads) on excised tumor xenograft are shown at 40× magnification, FIG. 11-1L. A significantly greater ($P=3.8\times10^{-8}$ by two-sample t-test) T/B ratio for ALL*-Cy5.5 (8.3±1.3) was found compared to QRH*-Cy5.5 (3.0±0.7) from n=8 tumors in n=8 tumors mice, FIG. 11-2L. FIG. 11-2A-K present data from the original experiment, showing the same results as FIG. 11-1A-J.

In the current studies, the affinity of ALL*-Cy5.5 peptide was 71.28 nM and the in vivo imaging peak time was 2 hours post injection. This short probe delivery time is an advantage for human clinical translational applications. Without being bound by theory, it is contemplated that the short delivery time can attributed to the addition of amino acid linker sequence, GGGSK, between targeting peptide sequence and the near-infrared dye Cy5.5, reducing steric hindrance from the dye moiety upon target binding. Moreover, ALL*-Cy5.5 probe has 1+ve overall charge (including linker sequence), 9 (out of 17, 53%) hydrophobic amino acids and 4 polar uncharged amino acids. Without being bound by theory, it is also contemplated that the charge and polarity of the probe could help hydrogen bond forming to improve solubility and distribution time of the probe.

Example 9

In Vivo Hand Held Dual-Axis Confocal Microscopic Imaging

GPC3 expression from human HCC xenograft tumors was evaluated in real time by collecting optical sections in vivo using a handheld 5.5 mm diameter dual axes confocal endomicroscope [64]. A solid-state diode laser (300 mW, CNI Laser Inc.) provided illumination at $\lambda_{ex}=671$ nm. A parabolic mirror focused the illumination and collection beams to overlap below the tissue surface with lateral and axial resolution of 2 and 5 µm, respectively. A compact, 3D monolithic scanner located in the distal tip provided large vertical displacements and wide angular deflections to produce images in the vertical (XZ) and horizontal (XY) planes with a FOV of 1000×430 and 1000×1000 µm², respectively.

NIR fluorescence is collected and passes through a band pass filter (FF01-716/40-25, Semrock) that transmits from 696-736 nm with >93% efficiency for detection with a photomultiplier tube (PMT, H7422PA-40, Hamamatsu) detector. The peptides were injected via the tail vain, and dissected away the skin overlying the tumor to gain access. The distal tip of the endomicroscope was placed in contact with the tumor using a drop of saline to couple the light. Laser power <2 mW on the tissue was used to avoid photobleaching. NIR fluorescence images were collected at 5 frames per sec. 3D volumetric images were reconstructed from a series of images collected in the vertical plane using Amira software (ver 5.4.3, FEI Corporation).

Figure 12:
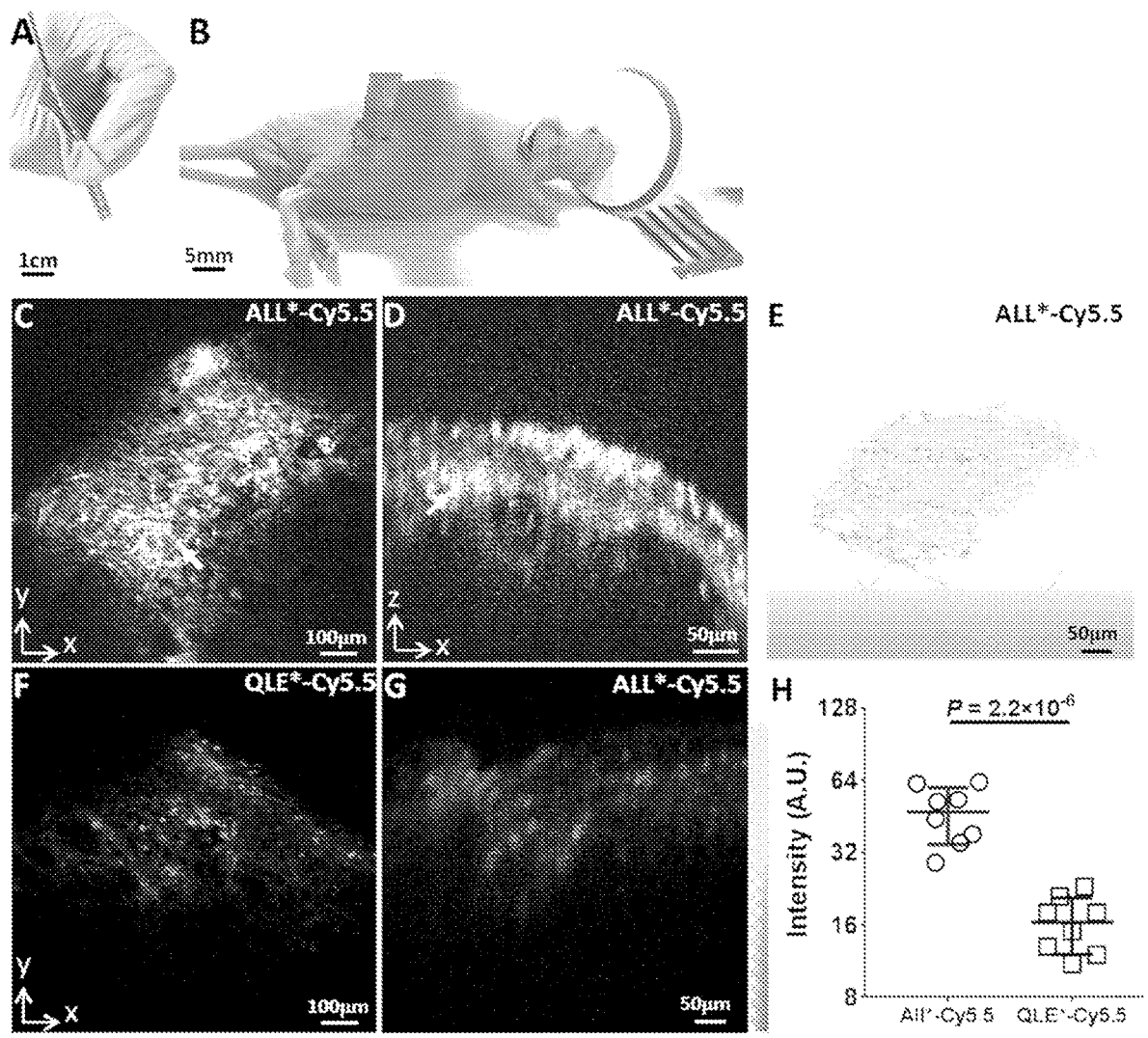
FIGS. 12A-H show in vivo optical imaging of HCC xenograft tumor. A) Handheld dual axes confocal endomicroscope was used to collect real-time in vivo images with sub-cellular resolution. B) The distal tip of instrument was placed in contact (inset) with the lesion in live tumor-bearing mouse. Strong uptake (arrow) of ALL*-Cy5.5 is seen in tumor on optical sections collected in the C) horizontal (1000×1000 μm2) and D) vertical (1000×430 μm2) planes, respectively. E) A series of vertical cross-section images were reconstructed into 3D MIP volume. F) Minimal staining was observed in xenograft tumor from control peptide QLE*-Cy5.5 in horizontal and G) vertical planes. H) 2.9-fold increase (47±13 vs 16±4, $P=2.2\times10-6$) in fluorescent intensity was observed in ALL*-Cy5.5 injected mice at tumor compared to control peptide QLE*-Cy5.5.

The probe was small enough to be comfortably held in the surgeon's hand during surgery, FIG. 12A, for in vivo imaging of biomarker expression. Its diameter was 5.5 mm and delivered 671 nm near-infrared laser at 2 mW. Mouse carrying HCC xenograft tumor overexpressing GPC3 was first injected with 250 μL 300 μM ALL*-Cy5.5 peptide intravenously and after 2 hours the probe was held in contact with exposed subcutaneous tumor to acquire in vivo peptide binding images, FIG. 12B. Images were collected in either the vertical or horizontal plane with 430 μm depth or 1000×1000 μm$^2$ area, respectively, at 5 frames per second. With measured lateral resolution of 2.49 μm and axial resolution of 4.98 μm, each peptide stained cell can be clearly seen (arrows). A reconstructed 3D MIP image reveals all the stained cells in the tumor. Strong uptake (arrows) of ALL*-Cy5.5 in tumor was captured on optical sections collected in the horizontal (1000×1000 μm$^2$, Video 1) FIG. 12C and vertical (1000×430 μm$^2$, Video 2) FIG. 12D planes, respectively. A series of vertical cross-section images were reconstructed into 3D MIP volume (Video 3), FIG. 12E. Minimal staining was observed in xenograft tumor from control peptide QLE*-Cy5.5 in the horizontal and vertical planes, FIG. 12F-G. Fluorescent signal of ALL*-Cy5.5 is significantly higher ($P=2.2\times10^{-6}$ on log-transformed data, 2.9-fold larger) than that of QLE*-Cy5.5, by two-sample t-test with n=8 mice in each group, FIG. 12H.

Example 10

Ex Vivo Microscopic Validation of GPC3 Over Expressed in Mouse Xenograft

Figure 13:
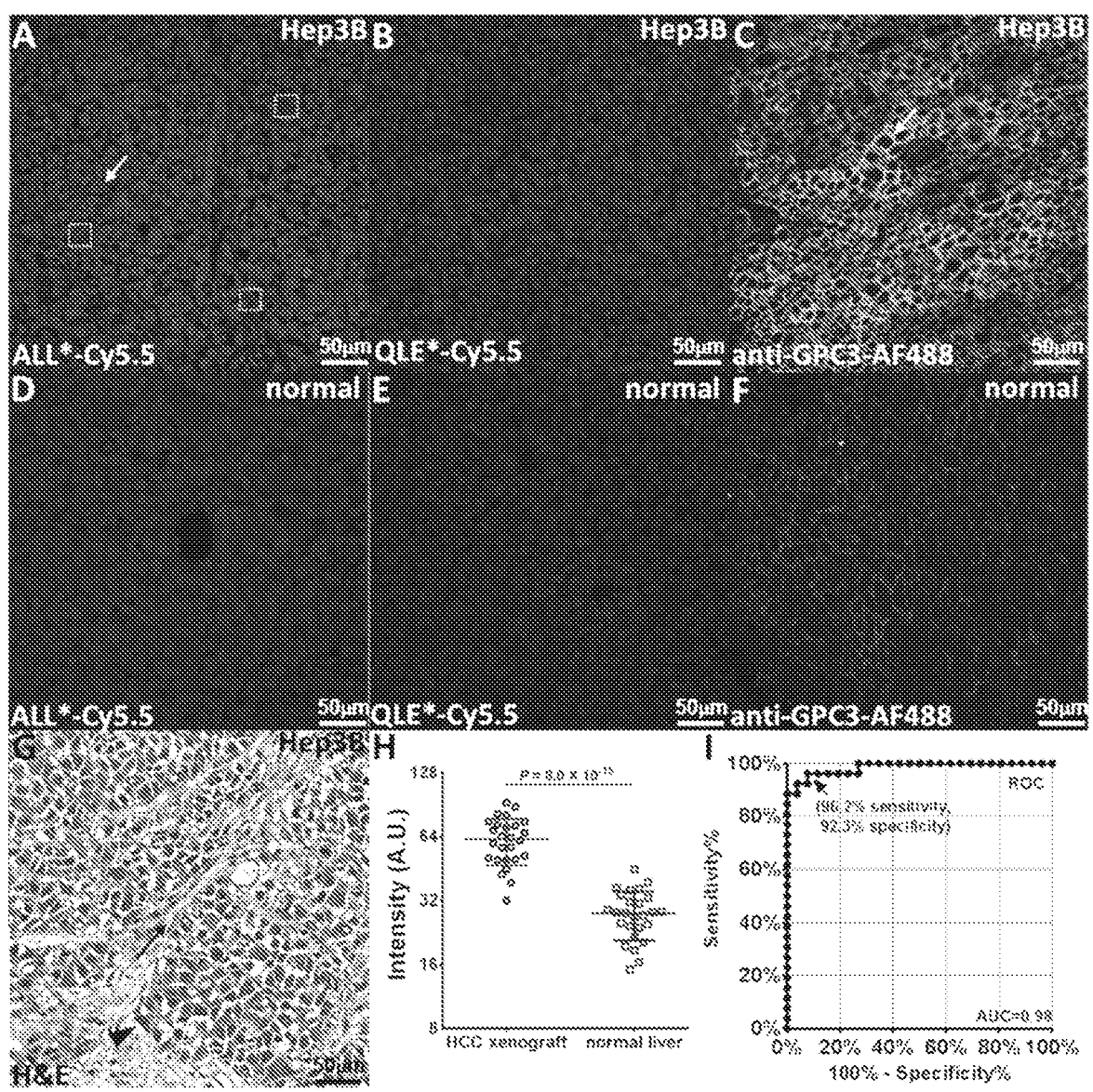
FIGS. 13A-I show validation of specific peptide binding to GPC3 overexpressed in mouse HCC xenograft tumors. Confocal microscopy of A) ALL*-Cy5.5 compared to B) QLE*-Cy5.5 to sections of Hep3B xenograft tumors. Fluorescence intensities were measured from sets of 3 (dashed white) boxes with dimensions of 20×20 μm2. C) Using a known antibody, overexpression of GPC3 on cell surface of Hep3B xenograft was confirmed (arrows) D-E) Minimal staining was observed with either ALL*-Cy5.5 or QLE*-Cy5.5 to normal liver F) low GPC3 expression was observed with anti-GPC3 antibody staining. G) Histology (H&E) of Hep3B xenograft showed features of enlarged nuclei (arrow) and highly invasive vasculature (arrowhead). H) Greater intensity from peptide binding to HCC than normal was found with 2.22-fold difference, P=8.0×10$^{-15}$ by two-sample t-test, n=26. I) The corresponding ROC curve shows 96.2% sensitivity and 92.3% specificity for distinguishing HCC from normal liver with an area under curve of AUC=0.98.
Figure 14:
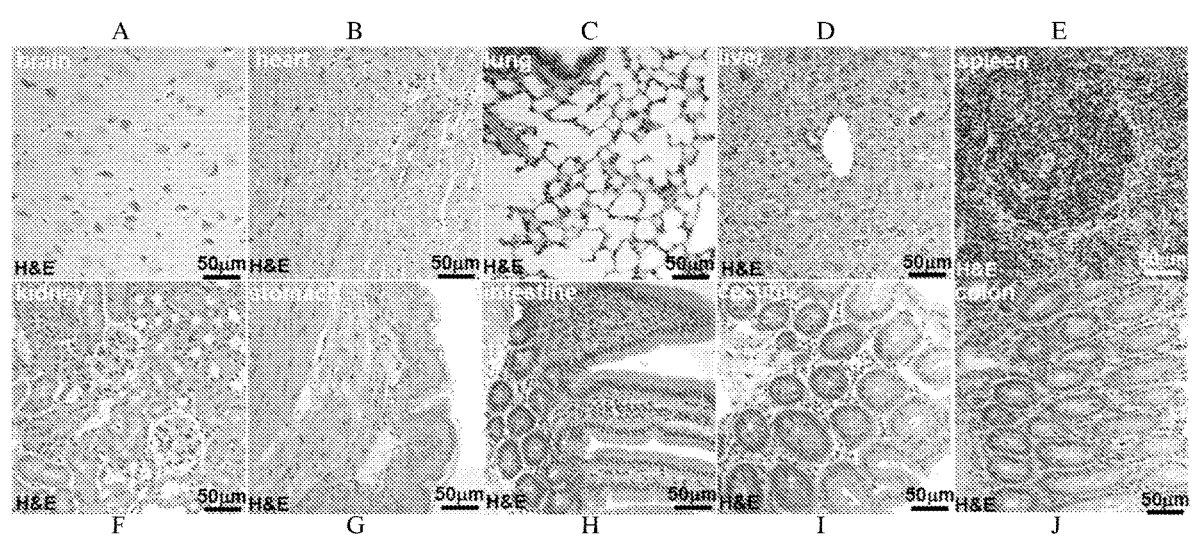
FIGS. 14A-J show histology of vital organs post-peptide administration. Mice bearing human HCC xenograft tumors were sacrificed 2 hours post-injection of ALL*-Cy5.5. No signs of acute peptide toxicity were observed in A) brain, B) heart, C) lung, D) liver, E) spleen, F) kidney, G) stomach, H) intestine, I) cecum, or J) colon.
Figure 18:
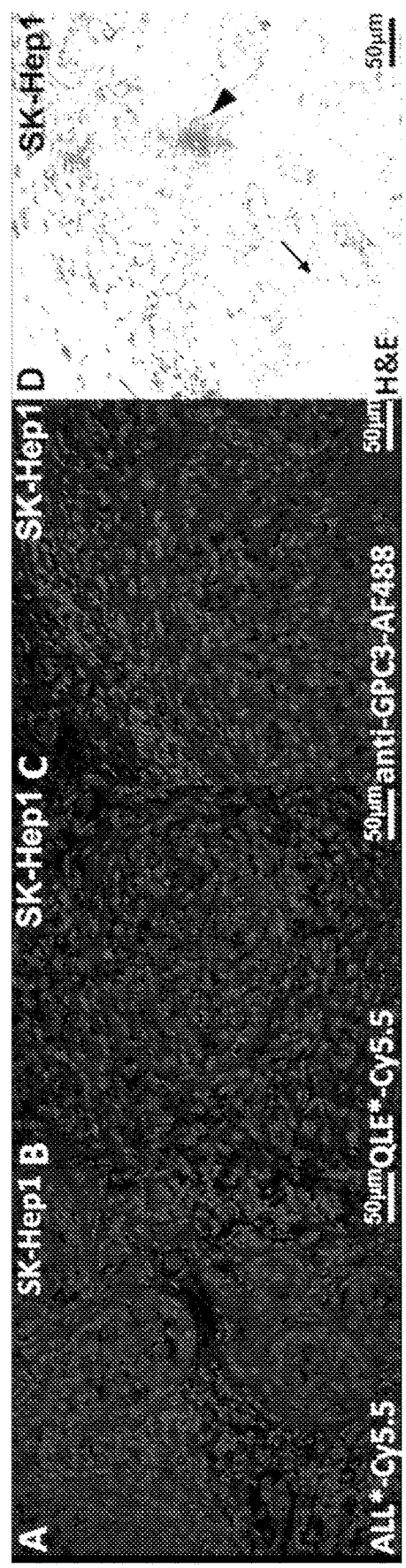
FIGS. 18A-D show immunostaining on GPC3 negative HCC xenograft tumor. A-B) No staining of ALL*-Cy5.5 and QLE*-Cy5.5 was observed to sections of SK-Hep1 xenograft tumors. C) With a known antibody, negative expression of GPC3 was confirmed in SK-Hep1 xenograft D) Histology (H&E) shows A nest of tumor cells with large irregular round nuclei (arrow) and infiltrating blood vessels lined with flattened endothelial cells (arrowhead) can be seen.

The specimens were also sectioned for collection of confocal images to perform microscopic validation of peptide binding ex vivo. We found increased cell surface staining of ALL*-Cy5.5 compared with QLE*-Cy5.5 to Hep3B xenograft (arrow), FIG. 13A,B. Overexpression of GPC3 on cell surface of Hep3B xenograft was confirmed with known antibody, FIG. 13C. Minimal staining was observed with ALL*-Cy5.5, QLE*-Cy5.5, and anti-GPC3 antibody on normal mouse liver, FIG. 13D-F. Histology (H&E) of Hep3B xenograft showed features of enlarged nuclei (arrow) and highly invasive vasculature (arrowhead) in Hep3B xenograft tumor sections, FIG. 13G. Greater intensity from peptide binding to HCC than normal was found with 2.22-fold difference, $P=8.0\times10^{-15}$ by paired t-test, n=26 tumors from 26 mice, FIG. 13H. The corresponding ROC curve showed 96.2% sensitivity and 92.3% specificity for distinguishing HCC from normal liver with an area under curve of AUC=0.98, FIG. 13I. No staining was observed for either peptide with SK-Hep1 xenograft, FIG. 18A-B, which had no GPC3 expression, FIG. 18C. Histology (H&E) showed a nest of tumor cells with large irregular round nuclei (arrow) and infiltrating blood vessels lined with flattened endothelial cells (arrowhead) can be seen, FIG. 18D.

Vital organs were harvested post peptide administration in mice to evaluate acute toxicity of peptide probe with histology observation. Mice bearing human HCC xenograft tumors were sacrificed 2 hours post-injection of ALL*-Cy5.5. No signs of acute peptide toxicity were seen in brain, heart, lung, liver, spleen, kidney, stomach, intestine, cecum, colon, FIG. 14A-J.

Example 11

Microscopic Validation on U.S. Patent Liver Biopsies

Specific peptide binding to human HCC was confirmed on patient biopsies (n=41) ex vivo from University of Michigan Hospital. In immunofluorescence analysis, ALL*-Cy5.5 showed negative staining to human normal liver tissue from specimens, FIG. 15A. Antibody staining of the same tissue confirmed minimal GPC3 expression, FIG. 15B. Binding by ALL*-Cy5.5 peptide and AF488-labeled anti-GPC3 antibody co-localized on normal liver specimen with Pearson's correlation coefficient of p=0.62, FIG. 15C. Co-stained regions were also imaged at 40×, FIG. 15D and 100× (dashed box in Panel D) magnifications, FIG. 15E. Minimal staining was observed in adenoma tissue with Pearson's correlation coefficient of p=0.63, FIG. 15F-J, and moderate diffuse staining was observed in cirrhotic liver tissue with Pearson's correlation coefficient of p=0.57, FIG. 15K-O. Strong intense staining with Pearson's correlation coefficient of p=0.66 was observed in HCC tissue, FIG. 15P-S. Cell surface staining (arrow) is shown in FIG. 15T.

Figure 15:
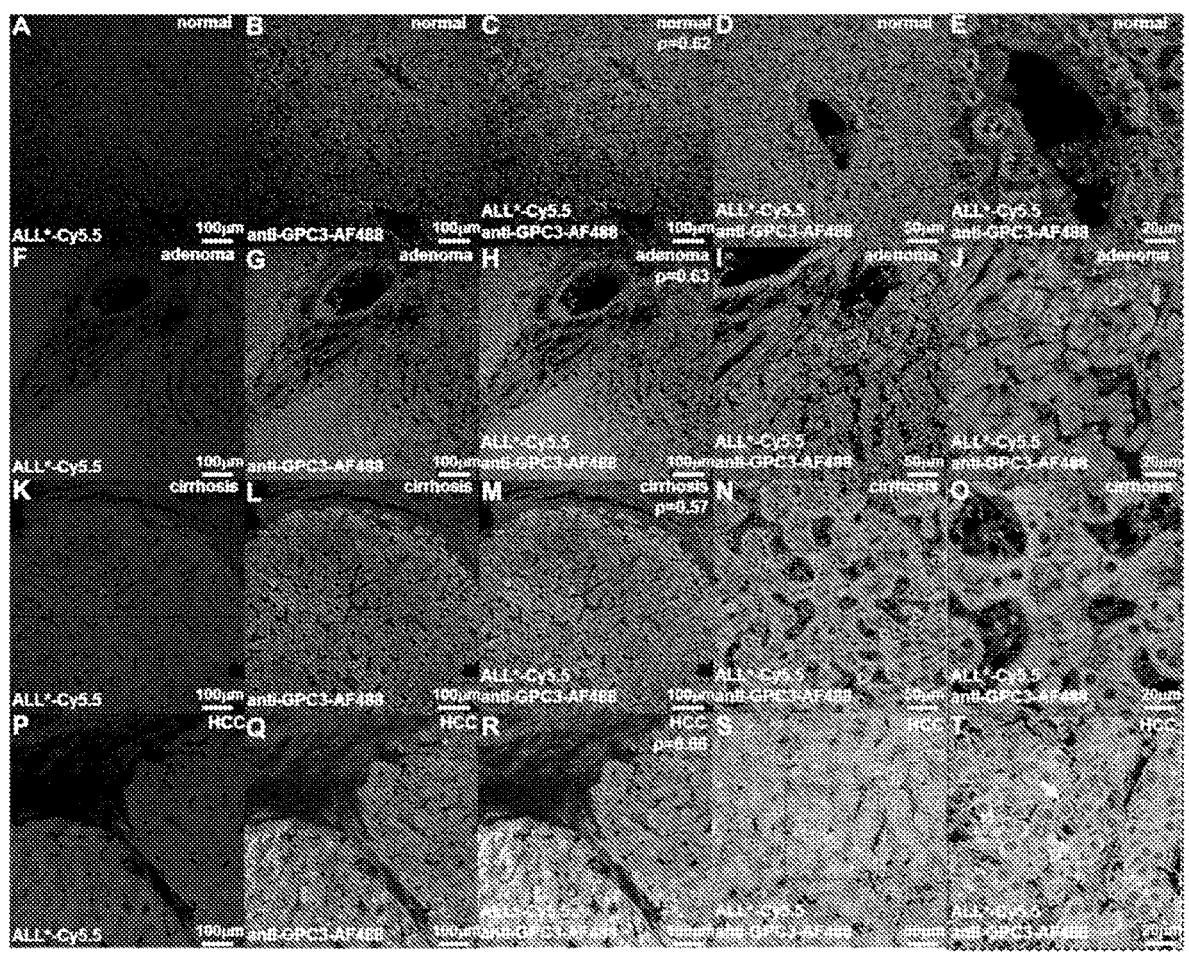
FIGS. 15A-W show specific peptide binding to human HCC ex vivo. A) On immunofluorescence (IF), ALL*-Cy5.5 shows negative staining to human normal liver tissue from specimens. B) Antibody staining of the same tissue confirmed minimal GPC3 expression. C) Binding by ALL*-Cy5.5 peptide and AF488-labeled anti-GPC3 antibody co-localizes on normal liver specimen with Pearson's correlation coefficient of ρ=0.62. Co-stained regions were also imaged at D) 40X and E) 100X (dashed box in D) magnifications. F-J) Minimal staining was observed in adenoma tissue with Pearson's correlation coefficient of ρ=0.63 and K-O) moderate diffuse staining was observed in cirrhotic liver tissue with Pearson's correlation coefficient of ρ=0.57. P-S) Strong intense staining with Pearson's correlation coefficient of ρ=0.66 was observed in HCC tissue T) showing cell surface staining (arrow). U) Quantitative comparison of ALL*-Cy5.5 binding to human HCC with normal liver, adenoma and cirrhosis tissue. We fit an ANOVA model with terms for 4 conditions and 41 patients (n=7 for normal and adenoma, n=12 for cirrhosis and n=15 for HCC) to log-transformed data and found a 3.43-fold greater (P=8.6×10$^{-10}$) signal for ALL*-Cy5.5 in HCC than normal, and 2.48-fold increase (P=2.7×10$^{-6}$) from adenoma and 2.05-fold increase (P=2.7×10$^{-6}$) from cirrhosis. V) The corresponding ROC curve shows 93% sensitivity at 88% specificity for distinguishing HCC from all non-HCC tissue with an area under curve of AUC=0.98. W) ROC curve shows 87% sensitivity at 100% specificity for distinguishing HCC from cirrhosis with an area under curve of AUC=0.97.
Figure 15:
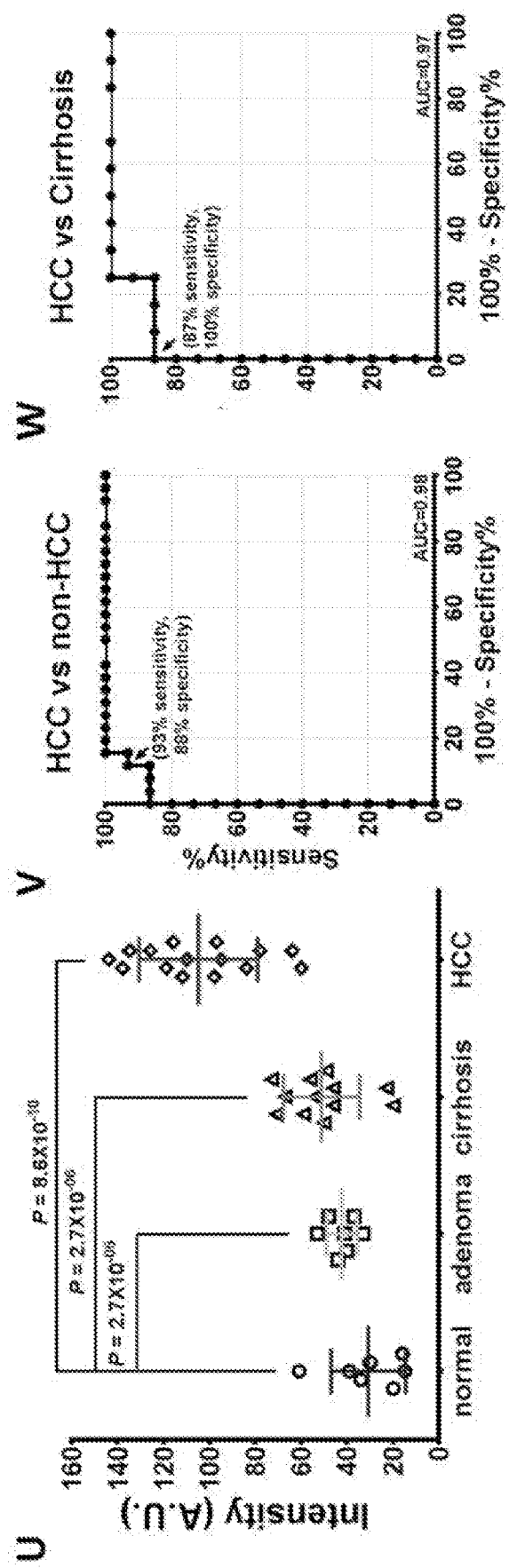

Quantitative comparison of ALL*-Cy5.5 binding to human HCC with normal liver, adenoma and cirrhosis tissue was summarized in FIG. 15U. An ANOVA model was applied with terms for 4 conditions and 41 patients (n=7 for normal and adenoma, n=12 for cirrhosis and n=15 for HCC) to log-transformed data and found a 3.43-fold greater ($P=8.6\times10^{-10}$) signal for ALL*-Cy5.5 in HCC than normal, and 2.48-fold increase ($P=2.7\times10^{-6}$) from adenoma and 2.05-fold increase ($P=2.7\times10^{-6}$) from cirrhosis. The corresponding ROC curve showed 93% sensitivity at 88% specificity for distinguishing HCC from all non-HCC tissue with an area under curve of AUC=0.98, FIG. 15V. ROC curve shows 87% sensitivity at 100% specificity for distinguishing HCC from cirrhosis with an area under curve of AUC=0.97, FIG. 15W.

Figure 16:
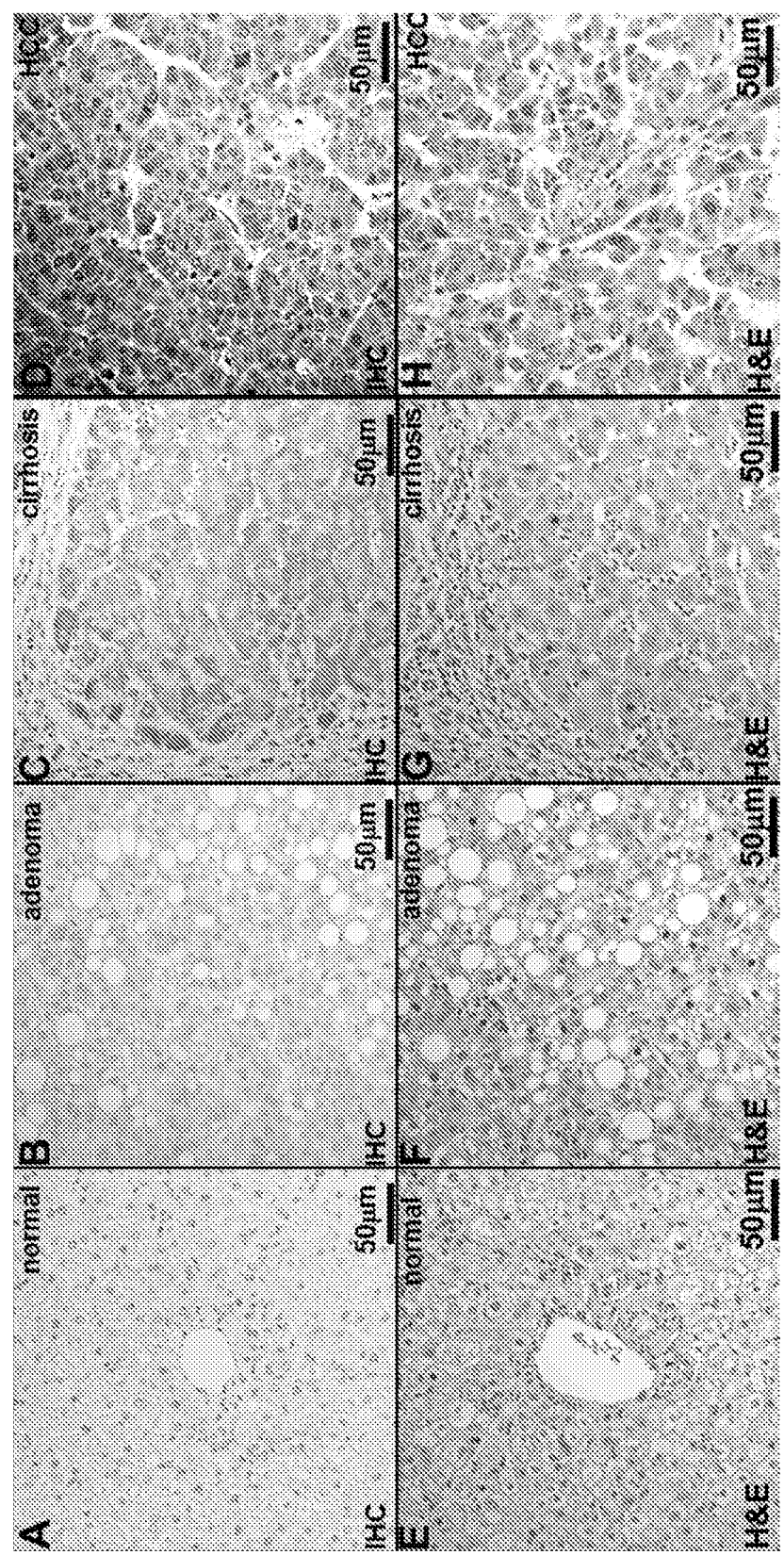
FIGS. 16A-H show immunohistochemistry (IHC) with anti-GPC3 antibody stains negative on A) normal liver, B) moderately on adenoma and C) cirrhosis human tissue. D) Intense staining was observed in HCC human tissue. Corresponding representative histology (H&E) for E) normal, F) adenoma, G) cirrhosis and H) HCC.

Immunohistochemistry (IHC) with anti-GPC3 antibody stained negative on normal liver, moderately on adenoma and cirrhosis human tissue, FIG. 16A-C. Intense staining was observed in HCC human tissue, FIG. 16D. FIG. 16E-H show corresponding representative histology (H&E) for normal, adenoma, cirrhosis and HCC. All 41 biopsies were diagnosed by pathologist and the patients' medical history and histology notes were recorded in FIG. 19.

Example 12

Binding of Specific Binding of GPC3 Peptide to HBV-Derived HCC in Vitro

Specific binding of the optimized GPC3 peptide reagent to human specimens of HBV-related HCC was demonstrated using immunofluorescence.

Formalin-fixed specimens of HBV-derived HCC from the bio-bank at the Peking University People's Hospital were used. The specimens were deparaffinized, and antigen retrieval was performed using standard methods. Specimens of HCC and non-tumorous liver were cut in 10 µm sections, and incubated with the ALL*-Cy5.5 peptide reagent at a concentration of 5 µM in 1× PBS for 15 min at RT. The sections were washed 3× with PBS and incubated overnight at 4° C. with a 1:1000 dilution of primary anti-GPC3 antibody (Santa Cruz Biotechnology, 1G12, sc-65443) overnight at 4° C. The sections were washed with PBS 3× and incubated with 1:500 dilution of Alexa Fluor 488-labeled secondary goat anti-rabbit antibody (Invitrogen) for 1 hour at RT. The sections were fixed with 4% PFA for 10 min. The sections were then mounted with ProLong Gold reagent containing DAPI (Invitrogen). Confocal fluorescence images were collected with DAPI, FITC and Cy5.5 filters. A Pearson's correlation coefficient will be measured to assess co-localization of peptide and antibody binding.

Figure 17:
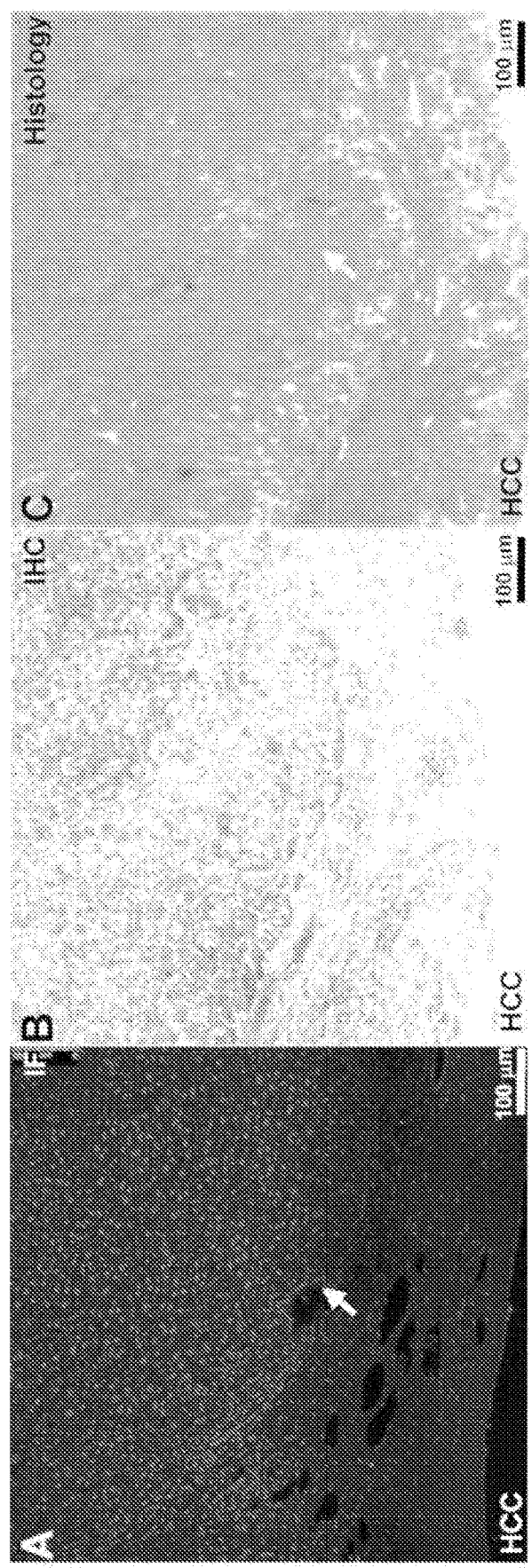
FIGS. 17A-C show binding of lead candidate GPC3 peptide to human HBV-derived HCC. A) On immunofluorescence (IF), strong binding of Cy5.5-labeled GPC3 peptide to representative section of HCC (arrow) is observed. B) On immunohistochemistry (IHC), strong staining of anti-GPC3 antibody to HCC (arrow) is seen on a serial section. C) Corresponding histology (H&E).

On confocal microscopy, increased signal is seen from the tumor (arrow) compared with adjacent non-tumor regions on immunofluorescence (IF), FIG. 17A. This result is supported by immunohistochemistry (IHC) performed on a serial section using anti-GPC3 antibody, FIG. 17B. Corresponding histology shows HCC (H&E), FIG. 17C.

Example 13

GPC3 Peptide-Labeled Polymeric Micelles Encapsulating Sorafenib

GPC3 peptide, with a maleimide functional group conjugated at the C-terminus via GGSK linker on the side chain of a lysine residue, is conjugated to octadecyl lithocholate and assembled with polyethylene glycol (PEG) (FIG. 20-1A, B) to form octadecyl lithocholate polymeric micelles as follows.

Octadecyl Lithocholate Micelles

Lithocholic acid (1.5 g, 4 mmol) and HOBt (1.5 g, 10 mmol) will be dissolved in N,N-dimethylformamide (DMF) (12 mL). DIC (1.5 mL, 10 mmol) will be added. After 10 min for activation, octadecyl amine (0.9 g, 3.3 mmol) will be added along with dichloromethane (DCM) 4 mL. The reaction will be allowed to stir overnight at room temperature (RT). The resulting product will be filtered and vacuum dried. Octadecyl lithocholate (573 mg, 0.91 mmol) will be dissolved in anhydrous DCM (15 mL). Catalytic amount of DMAP will be added. Succinic anhydride (90.9 mg, 0.91 mmol) and DIEA (950 µL, 5.45 mmol) will be added and the reaction was allowed to run overnight at RT. The solvent was evaporated under $N_2$ and the resulting product will be vacuum dried.

Pegylation: Pegylation will be performed by dissolving succinyl octadecyl lithocholate (64.2 mg, 0.09 mmol) in DCM 2.5 mL and DMF 1 mL. HOBt (41.3 mg, 0.27 mmol) will be added, followed by addition of DIC (50 µL, 0.27 mmol). Methoxy PEG amine (143 mg, 0.05 mmol) will be added after 10 min for activation. The reaction will be allowed to stir overnight at 40° C. The solvent will be partially removed under $N_2$ and the resulting product will be precipitated in cold diethyl ether, centrifuged, and vacuum dried. Succinyl octadecyl lithocholate will be conjugated with thiol PEG amine in the same manner.

Peptide labeling: Thiol pegylated octadecyl lithocholate (74.8 mg, 0.02 mmol) and TCEP (9.68 mg, 0.03 mmol) will be dissolved in phosphate buffer pH 8.0 (15 mL). The maleimide GPC3 peptide (0.02 mmol) will be added and the reaction will be allowed to run overnight at RT. The resulting product will be dialyzed against 3× changes of water and lyophilized.

Drug encapsulation: Polymeric micelles form by self-assembly when the critical micelle concentration (CMC) is reached as intermolecular forces aggregate the individual polymers. Sorafenib will be added to the polymer solution for partitioning in the core prior to aggregation. The polymers will be sonicated until fully dispersed. The polymeric micelle solution will then be centrifuged to remove insoluble materials, and GPC3-labeled polymeric micelles encapsulating sorafenib in the supernatant will be separated. Transmission electron microscopy (TEM) was used to show the nanostructure of peptide-labeled polymeric micelles (FIG. 20-1C).

D-α Tocopherol Succinate Micelles

Figures 1, 20:
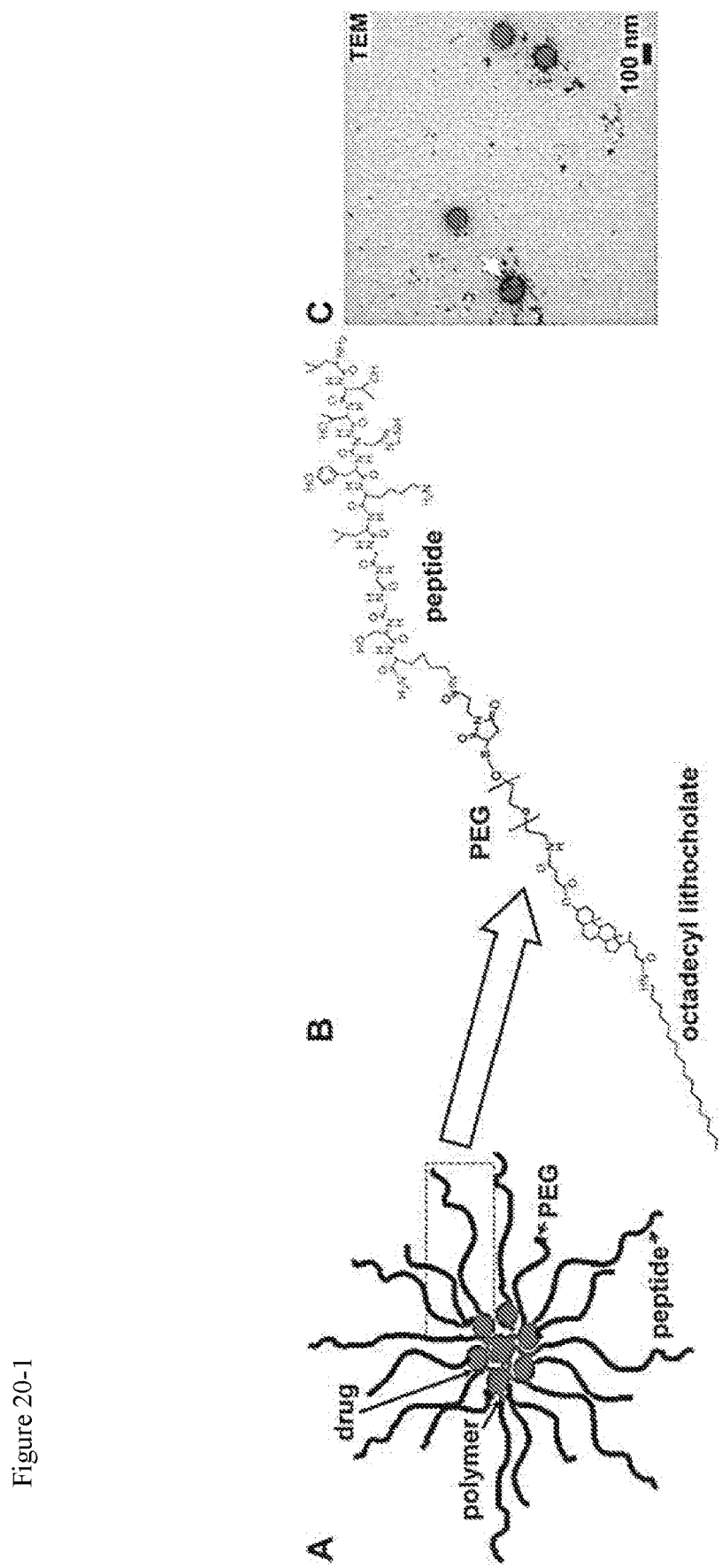
Figures 2, 20:
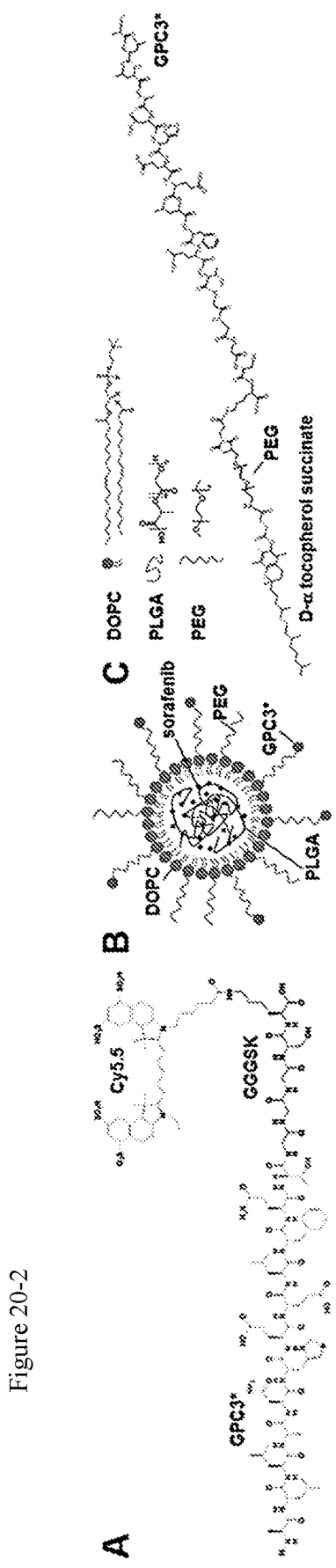

Alternatively, the GPC3 peptide is attached to a Cy5.5 fluorophore via a GGGSK linker on the C-terminus to prevent steric hindrance, hereafter GPC3*-Cy5.5 (FIG. 20-2A) and used to generate D-α tocopherol succinate polymeric micelles as follows (FIG. 20-2B). Cy5.5 was chosen because of its high quantum yield, photo-stability, and compatibility for use with confocal microscopy. The peptides were synthesized with >95% purity by HPLC, and the experimental mass-to-charge (m/z) ratio was confirmed by mass spectrometry. The peptides were lyophilized for storage, and stability over time is monitored every 3 months by HPLC and mass spec.

Pegylation—Pegylation will be performed by dissolving D-α tocopherol succinate (47.8 mg, 0.09 mmol) in dichloromethane (DCM) 2.5 mL and dimethylformamide (DMF) 1 mL. 1-hydroxybenzotriazole (HOBt) (41.3 mg, 0.27 mmol) will be added, followed by addition of N, N'-diisopropylcarbodiimde (DIC) (50 µL, 0.27 mmol). Thiol PEG amine (177 mg, 0.05 mmol) will be added after 10 min for activation. The reaction will be allowed to stir overnight at 40° C. The solvent will be partially removed under $N_2$ and the resulting product will be precipitated in cold diethyl ether, centrifuged, and vacuum dried.

Peptide labeling—Thiol D-α-tocopherol polyethylene glycol succinate (83.4 mg, 0.02 mmol) and TCEP (9.68 mg, 0.03 mmol) and tris (2-carboxyethyl) phosphine HCl (TCEP) (9.68 mg, 0.03 mmol) will be dissolved in phosphate buffer pH 8.0 (15 mL). The maleimide GPC3 peptide (0.02 mmol) will be added, and the reaction will be allowed to run overnight at RT. The resulting product will be dialyzed against 3 changes of water and lyophilized, FIG. 20-2C.

Preparation of nanocarrier—Polymeric nanoparticles form by single-step self-assembly. Either sorafenib or Cy5.5 will be added to PLGA (poly (lactic-co-glycolic acid)) and DOPC (1,2-Dioleoyl-sn-glycero-3-phosphocholine) in acetonitrile in oil phase for partitioning in the nanocarrier core prior to aggregation. Cy5.5 will be used as an optical reporter for the in vivo pharmacokinetic studies. The nanocarriers will be formed by adding oil phase slowly to water phase containing either PEG and/or the optimized GPC3-labeled PEG. The system will be sonicated until fully dispersed. The organic solvent will be removed by nitrogen purging. The polymeric nanocarrier solution will then be centrifuged to remove any insoluble materials, and the GPC3-labeled polymeric nanocarriers encapsulating either sorafenib or Cy5.5 in the supernatant will be separated.

Example 14

Inducing regression of xenograft tumors in a pre-clinical xenograft model of HCC Develop HCC xenograft tumors: We will first evaluate efficacy of the GPC3-peptide labeled polymeric micelles using cultured human HCC cells. ~5×10$^6$ human Hep3B (GPC3+) and SK-Hep1 (control) cells will be grown and diluted in growth factor reduced matrigel matrix. Both cell lines become tumorigenic after subcutaneous inoculatation in nude mice. The cells will be injected into either flank of nude athymic mice (nu/nu, Jackson Labs) at 4-6 weeks of age with weight between 20-25 gm.

Validate specific binding of GPC3 peptide: We will use a small animal laparoscope that has been adapted to collect fluorescence images. Imaging will be performed after surgically exposing the skin above the HCC xenograft tumor. Fluorescence will collected after intravenous injection of either Cy5.5-labeled GPC3 peptide reagent or scrambled (control) peptide (150 mM, 200 µL) using 671 nm excitation.

Measure target-to-background ratio for HCC tumors: Regions of interest (ROI) over the HCC tumor and adjacent normal (background) tissues will be drawn using custom Matlab software. The mean and standard deviation will be calculated from pixels within region boundaries. Target-to-background ratios will be calculated from these processed regions (mean signal from tumor ROI divided by mean signal from background ROI).

Example 15

GPC3 Peptide-Labeled Polymeric Micelle Therapy

We will study n=8 animals in n=4 treatment groups (total n=32): 1) GPC3 peptide-labeled and 2) unlabeled polymeric micelles encapsulating sorafenib, 3) free sorafenib, and 4) control (NSS). We will administer therapy to each group of animals daily at a dose of 5 mg/kg via an intraperitoneal (i.p.) injection for 35 days beginning at 6 weeks post-inoculation of cells when HCC tumors will be ~1 cm in size. The mice will be weighed daily over the duration of therapy.

Monitor tumor regression: Tumor dimensions will be measured daily with ultrasound. The transducer (40 MHz) will be used in B-mode, and translated along the length and width of the tumor. Multiple images will be taken in each direction to calculate tumor volume. T1 weighted MRI may be used if the tumors are too small to be seen by ultrasound. We will use a linear mixed effects regression model to assess the efficacy for GPC3 peptide-labeled polymeric micelles encapsulating sorafenib to induce regression of HCC tumor size. Interactions among treatment groups and over time will be estimated in this model for tumor regression rate.

Assess toxicity of polymeric micelles: After completion of therapy, all animals will be euthanized. Whole blood will be evaluated using a standard panel of labs, including hematology, chemistry, and coagulation factors. Tissues will be microscopically examined by necropsy, including bone with bone marrow (femur, sternum), brain (cerebrum, midbrain, cerebellum, medulla, pons), esophagus, heart, kidney, liver, lung with bronchi, lymph nodes (mesenteric), small intestine (duodenum, ileum, jejunum), spleen, stomach (glandular, non-glandular) and thymus.

Patient-derived xenograft model of HCC: We will evaluate efficacy of the optimized GPC3-peptide labeled polymeric micelles encapsulating sorafenib to induce regression in heterogeneous tumors that have clinically relevant GPC3 expression levels found in a broad patient population. Fresh surgical specimens will be obtained from n=10 patients with HBV-derived HCC who undergo hepatectomy. The specimens will be rinsed in PBS to remove blood and then placed in RPMI 1640 tissue culture media on ice. The specimens will be taken to the Experimental Animal Center within 30 min. The tumors will be cut into small pieces with sizes ranging between 1 to 2 mm$^3$. The specimens will be minced into fine fragments that are small enough to pass through an 18-gauge needle. Male athymic BALB/c nu/nu mice between 6 to 8 weeks of age with weight between 15 to 25 gm will be obtained from the Beijing Vital River Company (equivalent of Charles River Laboratories). Anesthesia will be administered to the mice using intra-peritoneal injection of chloral hydrate 0.43 mg/kg. Homogenized HCC tissue will be mixed 1:1 (v/v) with Matrigel to provide a total volume of 0.2 mL per injection. The tissue mixture will be injected subcutaneously in both flanks of the mice. The needle will be withdrawn slowly over 10 sec. For each tumor, n=6-8 mice will be injected. The control group will be injected with a mixture of PBS and Matrigel. The size of the patient-derived xenografts will be monitored daily with vernier calipers and ultrasound, and tumor volume will be calculated as described above. Therapy will be administered as described above to n=4 treatment groups: 1) GPC3-labeled and 2) unlabeled polymeric micelles encapsulating sorafenib, 3) free sorafenib, and 4) control (NSS). We will use a linear mixed effects regression model to assess differences in regression of HCC tumors, and evaluation of toxicity will be performed, as described above.

Perform biostatistical analysis: All data collected will be tested first for normality. A one-way, paired (or unpaired) t-test will be used to compare data between 2 groups. A one-way ANOVA or non-parametric Kruskal-Wallis will be used to compare data among more than 2 groups. A comparison will be considered significant if $P<0.01$ to adjust for multiple comparisons. If there is at least one difference between treatment groups, multiple comparisons will be used to search for pairwise differences. Tukey's multiple comparison test will be used to find pairwise differences after ANOVA analysis. Dunn's multiple comparison test will be used to find pairwise differences after Kruskal-Wallis. For animal weights, one random effect will be used to determine correlation among data from the same animal. All statistical computations will be processed using either Graphpad Prism or custom Matlab software.

While the present invention has been described in terms of specific embodiments, it is understood that variations and modifications will occur to those skilled in the art. Accordingly, only such limitations as appear in the claims should be placed on the invention.

All documents cited in this application are hereby incorporated by reference in their entirety, with particular attention to the disclosure for which they are referred.

We claim:

1. A reagent comprising a glypican-3-specific peptide ALLANHEELFQT (SEQ ID NO: 1), ALLANHEELF (SEQ ID NO: 2), or VGVESCASRCNN (SEQ ID NO: 5), or a multimer form of the peptide,
wherein the peptide specifically binds to glypican-3 and wherein at least one detectable label, at least one therapeutic moiety, or both, are attached to the peptide or a multimer form of the peptide.

2. The reagent of claim 1 comprising at least one detectable label attached to the peptide.

3. The reagent of claim 2 wherein the detectable label a microscopy, photoacoustic, ultrasound, PET, SPECT, or magnetic resonance imaging label.

4. The reagent of claim 3 wherein the microscopy label is fluorescein isothiocyanate (FITC), Cy5, Cy5.5, or IRdye800.

5. The reagent of claim 1 wherein the multimer form of the peptide is a dimer formed with an aminohexanoic acid linker.

6. The reagent of claim 2 wherein the detectable label is attached to the peptide by a peptide linker.

7. The reagent of claim 6 wherein a terminal amino acid of the linker is lysine.

8. The reagent of claim 7 wherein the linker comprises the sequence GGGSK set out in SEQ ID NO: 7.

9. The reagent of claim 1 comprising at least one therapeutic moiety attached to the peptide.

10. The reagent of claim 9 wherein the therapeutic moiety is chemotherapeutic agent.

11. The reagent of claim 9 wherein the therapeutic moiety is a micelle.

12. The reagent of claim 10 wherein the micelle is an octadecyl lithocholate micelle.

13. The reagent of claim 12 wherein the micelle is pegylated.

14. The reagent of claim 10 wherein the micelle encapsulates sorafenib.

15. A composition comprising the reagent of claim 1 and a pharmaceutically acceptable excipient.

16. A method for detecting hepatocellular carcinoma in a patient comprising the steps of administering the reagent of claim 1 to the liver of the patient and detecting binding of the reagent to hepatocellular carcinoma cells.

17. A method of determining the effectiveness of a treatment for hepatocellular carcinoma in a patient comprising the step of administering the reagent of claim 1 to the patient, visualizing a first amount of cells labeled with the reagent, and comparing the first amount to a previously-visualized second amount of cells labeled with the reagent,
wherein a decrease in the first amount cells labeled relative to the previously-visualized second amount of cells labeled is indicative of effective treatment.

18. A method for delivering a therapeutic moiety to hepatocellular carcinoma cells of a patient comprising the step of administering the reagent of claim 9 to the patient.

19. A kit for administering the composition of claim 15 to a patient in need thereof, said kit comprising the composition of claim 15, instructions for use of the composition and a device for administering the composition to the patient.

20. A peptide consisting of the amino acid sequence ALLANHEELFQT (SEQ ID NO: 1), ALLANHEELF (SEQ ID NO: 2), or VGVESCASRCNN (SEQ ID NO: 5).

* * * * *

UNITED STATES PATENT AND TRADEMARK OFFICE
CERTIFICATE OF CORRECTION

PATENT NO. : 11,248,022 B2
APPLICATION NO. : 16/491117
DATED : February 15, 2022
INVENTOR(S) : Juan Zhou et al.

Page 1 of 1

It is certified that error appears in the above-identified patent and that said Letters Patent is hereby corrected as shown below:

In the Claims

At Column 31, Line 21, "glypican-3 and" should be -- glypican-3, and --.

At Column 31, Line 27, "a" should be -- is a --.

Signed and Sealed this
Thirteenth Day of September, 2022

Katherine Kelly Vidal
*Director of the United States Patent and Trademark Office*